US010016431B2

(12) United States Patent
Scheurer et al.

(10) Patent No.: US 10,016,431 B2
(45) Date of Patent: Jul. 10, 2018

(54) SOLID PHARMACEUTICAL COMPOSITIONS COMPRISING BIOPTERIN DERIVATIVES AND USES OF SUCHCOMPOSITIONS

(71) Applicant: VASOPHARM GMBH, Wuerzburg (DE)

(72) Inventors: Peter Scheurer, Randersacker (DE); Frank Tegtmeier, Bielefeld (DE); Reinhard Schinzel, Gerbrunn (DE)

(73) Assignee: VASOPHARM GMBH, Wuerzburg (DE)

( * ) Notice: Subject to any disclaimer, the term of this patent is extended or adjusted under 35 U.S.C. 154(b) by 0 days.

(21) Appl. No.: 15/584,890

(22) Filed: May 2, 2017

(65) Prior Publication Data

US 2017/0296543 A1 Oct. 19, 2017

Related U.S. Application Data

(63) Continuation of application No. 14/913,665, filed as application No. PCT/EP2015/056824 on Mar. 30, 2015, now Pat. No. 9,895,372.

(30) Foreign Application Priority Data

Mar. 31, 2014 (EP) .................... 14162727

(51) Int. Cl.
| | | |
|---|---|---|
| *A01N 43/58* | (2006.01) | |
| *A01N 43/60* | (2006.01) | |
| *A61K 31/50* | (2006.01) | |
| *A61K 31/495* | (2006.01) | |
| *A61K 31/519* | (2006.01) | |
| *A61K 47/02* | (2006.01) | |
| *A61K 9/19* | (2006.01) | |
| *A61K 31/4985* | (2006.01) | |
| *A61K 9/00* | (2006.01) | |

(52) U.S. Cl.
CPC .......... *A61K 31/519* (2013.01); *A61K 9/0019* (2013.01); *A61K 9/19* (2013.01); *A61K 31/4985* (2013.01); *A61K 47/02* (2013.01)

(58) Field of Classification Search
CPC .................................................. A61K 31/519
USPC ...................................................... 514/249
See application file for complete search history.

(56) References Cited

U.S. PATENT DOCUMENTS

| 5,922,713 A | 7/1999 | Werner | |
| 8,222,238 B2 * | 7/2012 | Doblhofer ............ | A61K 31/519 514/183 |
| 9,382,252 B2 * | 7/2016 | Doblhofer ............ | A61K 31/519 |
| 9,422,289 B2 * | 8/2016 | Doblhofer ............ | A61K 31/519 |
| 2012/0128581 A1 | 5/2012 | Metcalfe et al. | |
| 2013/0053445 A1 | 2/2013 | Jiang et al. | |

FOREIGN PATENT DOCUMENTS

| EP | 0906913 B1 | 5/2001 |
| WO | 2004084906 A1 | 10/2004 |
| WO | 2006055511 A2 | 5/2006 |

OTHER PUBLICATIONS

Bastin et. al. Organic Process Research & Development 2000, 4, 427-435.*
Stahl, et. al. Handbook of Pharmaceutical Salts, (2002), 1-374.*
Office Action issued in related Colombian patent application No. 2016-0002524 dated Dec. 7, 2017—incl Engl lang transl.
Lundblad, List of Buffers in Biochemistry and Molecular Biology Compendium. CRC Press, Jun. 2007:p. 351.
Hanaya et al., Pteridines CV; Selective N(3)-and O4-Alkylation of L-Biopterin : A Convenient Synthesis of 3-and O4-Methyl-L-biopterin and the Versatile N2-(N,N-dimethylaminomethylene)-N(3)-p-nitrophenethyl-Protected L-Biopterin. Pteridines 1995;6(1):1-7.
Lockart and Pfleiderer et al., Pteridines, XCV; Synthesis of New N-5-Acyl-5,6,7,8-tetrahydropterins. Pteridines 1989;1(4):199-210.
Terpolilli et al., The Novel Nitric Oxide Synthase Inhibitor 4-amino-tetrahydro-L-biopterine Prevents Brain Edema Formation and Intracranial Hypertension following Traumatic Brain Injury in Mice. J Neurotrauma. Nov. 2009;26(11):1963-1975.
Werner et al., Identification of the 4-amino analogue of tetrahydrobiopterin as a dihydropteridine reductase inhibitor and a potent pteridine antagonist of rat neuronal nitric oxide synthase. Biochem J. 1996;320(Pt 1):193-196.
Office Action issued by the USPTO in U.S. Appl. No. 14/913,665 dated May 18, 2017.

* cited by examiner

*Primary Examiner* — Jeffrey H Murray
(74) *Attorney, Agent, or Firm* — TechLaw LLP; Sam K. Tahmassebi

(57) ABSTRACT

The present invention relates to a method of treating a disease in a subject, comprising administering to a subject in need thereof a solid pharmaceutical composition biopterin derivatives.

17 Claims, 4 Drawing Sheets

| Test Item | Specification | Storage Period in month | | | | | | | | |
|---|---|---|---|---|---|---|---|---|---|---|
| | | 0 | 3 | 6 | 9 | 12 | 18 | 24 | 36 |
| Appearance | White to pale red or brown lyophilized powder | complies | complies | complies | complies | complies | complies | complies | complies |
| Identification (HPLC) | Coelusion with reference substance | complies | complies | complies | complies | complies | complies | complies | complies |
| Assay (HPLC) (calculated on anhydrous and chloride-free basis | 650 ± 60mg | 645 mg | 649 mg | 634 mg | 660 mg | 684 mg | 658 mg | 686 mg | 694 mg |
| — (6R)—4-Amino-5,6,7,8-tetra-hydro-L-biopterin [% area] | 55.5 ± 3.0 | 54.6 | 54.6 | 55.0 | 54.6 | 54.4 | 55.1 | 54.8 | 54.6 |
| — (6S)—4-Amino-5,6,7,8-tetra-hydro-L-biopterin [% area] | 40.0 ± 3.0 | 41.5 | 41.6 | 41.3 | 41.6 | 41.4 | 41.8 | 41.5 | 41.4 |

FIG.3

| | | | | | | | | | |
|---|---|---|---|---|---|---|---|---|---|
| Related substances (HPLC)*: A [%area] B [%area] C [%area] | ≤ 4.5 ≤ 1.0 ≤ 1.0 | 2.8 0.2 0.3 | 2.5 0.2 0.3 | 2.5 0.2 0.1 | 2.8 0.2 0.2 | 3.0 0.2 0.1 | 2.5 0.2 0.1 | 2.8 0.2 0.2 | 2.8 0.2 0.3 |
| Further related substances, each [% area] | ≤ 0.6 | complies | complies | complies | complies | complies | complies | complies | complies |
| Further related substances, total [% area] | ≤ 2.0 | 0.7 | 0.8 | 0.9 | 0.6 | 0.9 | 0.3 | 0.2 | 0.6 |
| Water (KF–titration) | 3.0 to 8.0 % | 5.0 % | 4.5 % | 5.1 % | 4.8 % | 4.8 % | 4.8 % | 4.8 % | 4.7 % |
| Sterility | No evidence of microbial growth | complies | N.T. | N.T. | N.T. | complies | N.T. | N.T. | complies |
| Endotoxins | ≤ 10 I.U./mg | complies | N.T. | N.T. | N.T. | complies | N.T. | N.T. | complies |
| Particles – Particles ≥ 10 μm – Particles ≥ 25 μm | ≤ 6000 / vial ≤ 600 / vial | 600/vial 3/vial | N.T. N.T. | N.T. N.T. | N.T. N.T. | 767/vial 7/vial | N.T. N.T. | N.T. N.T. | 115/vial 1/vial |
| Reconstituted Solution§ – Dissolution Time – Appearance | Max 2 min Clear yellowish solution without visible particles | complies complies | complies complies | complies complies | complies complies | complies complies | complies complies | complies complies | complies complies |
| – pH – Osmolality [mosmol/kg] | 6.5 to 7.6 260 to 320 | 7.3 303 | 7.3 295 | 7.3 315 | 7.4 305 | 7.3 320 | 7.3 300 | 7.3 298 | 7.4 305 |

N.T.: Not Tested;
§: Reconstituted in 50 mL WFI
* A: 4–Amino–7,8–dihydro–L–biopterin; B: Σ (6R)–5,6,7,8–Tetrahydro–L–biopterin and (6S)–5,6,7,8–Tetrahydro–L–biopterin; C: Σ 1–[(6R)–2,4Diamino–5,6,7,8–tetrahydropteridin–6–yl]propanol and 1–[(6S)–2,4–Diamino–5,6,7,8–tetrahydropteridin–6–yl]propanol

FIG.3 (cont')

SOLID PHARMACEUTICAL COMPOSITIONS COMPRISING BIOPTERIN DERIVATIVES AND USES OF SUCH COMPOSITIONS

CROSS-REFERENCE TO RELATED APPLICATIONS

The present application is a continuation of U.S. patent application Ser. No. 14/913,665 filed under 35 U.S.C. § 371 as the U.S. national phase of International Application No. PCT/EP2015/056824, filed Mar. 30, 2015, which designated the U.S. and claims the benefit of priority to European Patent Application No. 14162727.3, filed Mar. 31, 2014, each of which is hereby incorporated in its entirety including all tables, figures and claims.

FIELD OF THE INVENTION

The present invention relates to solid pharmaceutical compositions comprising biopterin derivatives as well as methods for obtaining such solid pharmaceutical compositions. The invention also relates to the solid pharmaceutical compositions of the invention for treating diseases.

BACKGROUND OF THE INVENTION

Biopterines and their derivatives are molecules of pharmaceutical interest. For example, tetrahydrobiopterin (BH4, sapropterin) has recently been approved for treatment of hyperphenylalaninaemia (HPA) in adult and pediatric patients of 4 years of age and over with phenylketonuria (PKU). For this purpose, tetrahydrobiopterin is formulated in the commercial drug (sold under the name Kuvan) as a dissolvable tablet with Mannitol (E421), Calcium hydrogen phosphate, anhydrous, Crospovidone type A, Ascorbic acid (E300), Sodium stearyl fumarate and Riboflavin (E101). See in this context also WO 2006/055511.

Other therapeutically promising biopterin compounds are 4-Amino-5,6,7,8-tetrahydro-L-biopterin and 4-Amino-7,8-dihydro-L-biopterin. Both compounds have been shown to exhibit properties different from that of other NO-inhibitors, making the compound potentially more suitable than "classical" arginine analogues (Werner et al., (1996). Biochemical Journal 320, 93-6 or U.S. Pat. No. 5,922,713). Both compounds have been shown to be effective in experimental TBI (see, for example, WO 2004/084906, U.S. Pat. No. 8,222,828, European Patent 0 906 913 or Terpolilli et al., J Neurotrauma. 2009; 26(11):1963-75). However, these biopterin derivatives have not yet been approved for medical treatment. Thus, there is a need to provide pharmaceutical compositions that are suitable for therapeutic applications in humans. Ideally, such a pharmaceutical composition should be easy to prepare, easy to use and yet stable—it is noted in this context that hydrogenated biopterin derivatives are sensitive against oxidization, when stored over a long time or when provided in solution.

It is thus an object of the present invention to provide a pharmaceutical composition containing biopterin derivatives that fulfils these needs.

SUMMARY OF THE INVENTION

This problem is solved by the embodiments of the invention as defined in the claims, described in the description, and illustrated in the Examples and Figures.

The present invention relates in one embodiment to a solid pharmaceutical composition (adapted for intravenous administration) comprising
a) a compound having the formula (I):

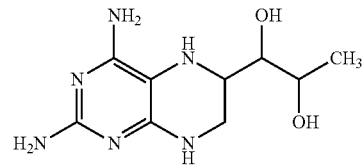

and/or a compound having the formula (II):

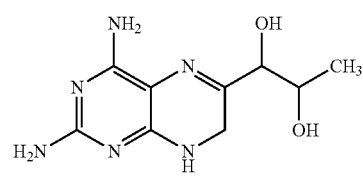

and
b) at least one phosphate salt.

The solid composition of the present invention may be "adapted for intravenous administration". This means that, after the solid composition is mixed with a pharmaceutically acceptable carrier, preferably a pharmaceutically acceptable fluid, e.g. water or buffer or any reconstitution fluid, a composition is obtained which directly as such can be used for intravenous application. Thus, after the mixing of the solid composition with the pharmaceutically acceptable carrier a ready-to-use composition, which is suitable for intravenous application, is obtained.

In one embodiment in the pharmaceutical composition of the present invention, the at least one phosphate salt is a sodium phosphate, a potassium phosphate or an ammonium phosphate. The phosphate salt may be selected from the group consisting of $Na_2HPO_4$ (water free), $Na_2HPO_4.2H_2O$, $Na_2HPO_4.7H_2O$, $Na_2HPO_4.12H_2O$, $NaH_2PO_4$ (water free), $NaH_2PO_4.H_2O$, $NaH_2PO_4.2H_2O$, $K_2HPO_4$ (water free) $K_2HPO_4.3H_2O$, $KH_2PO_4$ (water free) and mixtures thereof.

In some embodiments of the pharmaceutical composition of the present invention, the phosphate salt is $Na_2HPO_4.2H_2O$ and the quantity of the $Na_2HPO_4.2H_2O$ present in the composition is chosen such that the molar ratio of the $Na_2HPO_4.2H_2O$ to compound (I) or compound (II) ranges from 0.04 to 0.4.

In further embodiments of the pharmaceutical composition of the present invention, the sodium phosphate is $NaH_2PO_4.2H_2O$, and the quantity of the $NaH_2PO_4.2H_2O$ present in the composition is chosen such that the molar ratio of the $NaH_2PO_4.2H_2O$ to compound (I) or compound (II) ranges from 0.01 to 0.09.

In other embodiments, the pharmaceutical composition of the present invention comprises two different sodium phosphate salts. Optionally, the two different sodium phosphate salts are $NaH_2PO_4.2H_2O$ and $Na_2HPO_4.2H_2O$.

In some embodiments of the pharmaceutical composition of the present invention, the quantity of the $NaH_2PO_4.2H_2O$ and $Na_2HPO_4.2H_2O$ present in the composition is chosen such that the molar ratio of both $NaH_2PO_4.2H_2O$ and $Na_2HPO_4.2H_2O$ to compound (I) or compound (II) ranges from 0.02 to 0.5.

In some embodiments of the pharmaceutical composition of the present invention, the quantity of the NaH$_2$PO$_4$.2H$_2$O and Na$_2$HPO$_4$.2H$_2$O present in the composition is chosen such that the molar ratio of each of NaH$_2$PO$_4$.2H$_2$O and Na$_2$HPO$_4$.2H$_2$O to compound (I) or compound (II) ranges from 0.02 to 0.5.

In further embodiments of the pharmaceutical composition of the present invention the compound (I) and/or the compound (II) are present as the free base.

In some embodiments of the pharmaceutical composition of the present invention the pharmaceutical composition is a lyophilized pharmaceutical composition.

In another embodiment of the pharmaceutical composition of the present invention, the compound (I) is a compound having the formula (Ia):

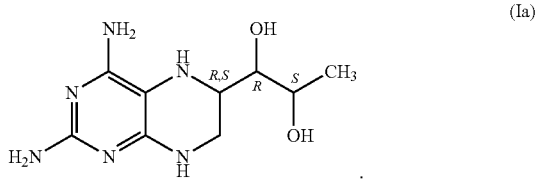

(Ia)

In another embodiment of the pharmaceutical composition of the present invention, the compound (II) is a compound having the formula (IIa):

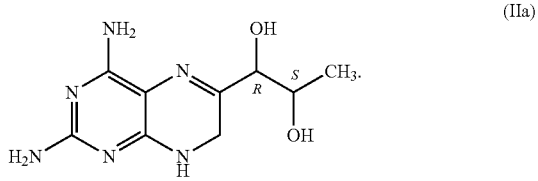

(IIa)

In some embodiments of the pharmaceutical composition of the present invention, the pharmaceutical composition comprises an additional pharmaceutical excipient.

In another embodiment of the pharmaceutical composition of the present invention, the additional pharmaceutical excipient is an inorganic salt. The inorganic salt can be selected from MgCl$_2$, CaCl$_2$, NH$_4$Cl, KCl, or NaCl, preferably the inorganic salt is NaCl.

In some embodiments of the pharmaceutical composition of the present invention, the quantity of the NaCl present in the composition of the present invention is chosen such that the molar ratio of the NaCl to compound (I) or compound (II) ranges from 1.5 to 4, preferably from 1.8 to 3.7.

In some embodiments the pharmaceutical composition of the present invention further comprises crystallization water.

In other embodiments the pharmaceutical composition of the present invention is adapted to be reconstituted in water. "Adapted to be reconstituted in water" means that (a dehydrated or concentrated) composition can be returned to the liquid state by adding water.

In further embodiments the pharmaceutical composition of the present invention is adapted for administration by infusion or injection.

In some embodiments of the pharmaceutical composition of the present invention the compound (I) is (6R)-4-Amino-5,6,7,8-tetrahydro-L-biopterin.

In further embodiments of the pharmaceutical composition of the present invention the compound (I) is (6S)-4-Amino-5,6,7,8-tetrahydro-L-biopterin.

In other embodiments of the pharmaceutical composition of the present invention the compound (I) is a diastereomeric mixture that comprises more (6R)-4-Amino-5,6,7,8-tetrahydro-L-biopterin than (6S)-4-Amino-5,6,7,8-tetrahydro-L-biopterin.

In some embodiments of the pharmaceutical composition of the present invention the quantity of the (6R)-4-Amino-5,6,7,8-tetrahydro-L-biopterin and the (6S)-4-Amino-5,6,7,8-tetrahydro-L-biopterin is chosen such that the ratio of the amount of (6R)-4-Amino-5,6,7,8-tetrahydro-L-biopterin to the (6S)-4-Amino-5,6,7,8-tetrahydro-L-biopterin ranges from 0.5 to 2, preferably around 1.3.

In further embodiments of the pharmaceutical composition of the present invention, a unit dosage of the composition contains 650±60 mg of the free base of 4-Amino-(6R,S)-5,6,7,8-tetrahydro-L-biopterin, 140±30 mg of water of crystallization, 70±7 mg disodium hydrogen phosphate dihydrate (Na$_2$HPO$_4$.2H$_2$O), 16.5±2 mg sodium dihydrogen phosphate dihydrate (NaH$_2$PO$_4$.2H$_2$O), and 350±30 mg sodium chloride (NaCl).

In other embodiments of the pharmaceutical composition of the present invention, a unit dosage of the composition contains 650±60 mg of the free base of 4-Amino-(6R,S)-5,6,7,8-tetrahydro-L-biopterin, 60±50 mg of water of crystallization, 70±7 mg disodium hydrogen phosphate dihydrate (Na$_2$HPO$_4$.2H$_2$O), 12±2.5 mg sodium dihydrogen phosphate dihydrate (NaH$_2$PO$_4$.2H$_2$O), and 350±30 mg sodium chloride (NaCl).

In some embodiments of the pharmaceutical composition of the present invention the composition comprises 1, 2, 3, 4, 5, 6, 7, or more additional compounds, wherein the additional compounds are selected from the group consisting of one or more of the compounds selected from the group consisting of 4-Amino-L-biopterin, (6R,S)-5,6,7,8-Tetrahydro-L-biopterin, 1-[(6R,S)-2,4-Diamino-5,6,7,8-tetrahydropteridin-6-yl]propanol, 1-[(6R,S)-2,4-Diamino-5,6,7,8-tetrahydropteridin-6-yl]propane, (1R,2S)-1-[(6R,S)-2-(Acetylamino)-4-amino-5,6,7,8-tetrahydropterin-6-yl]-1,2-diacetoxy-propane, 2,4-Diamino-7,8-dihydropteridine, 2,4-Diaminopteridine.

The present invention also relates to a use of a lyophilized pharmaceutical composition of the present invention for the treatment of a disease. In some embodiments, the disease is selected from the group consisting of a traumatic brain injury, non-traumatic brain injury, preferably stroke or meningitis, elevated cranial pressure, secondary brain injury.

Also, the present invention relates to a lyophilized pharmaceutical composition for use in the treatment of a disease. In some embodiments, the disease is selected from the group consisting of a traumatic brain injury, non-traumatic brain injury, preferably stroke or meningitis, elevated cranial pressure, secondary brain injury.

The present invention further relates to a method for preparing a lyophilized solid pharmaceutical composition (adapted for intravenous administration) comprising
a) a compound having the formula (I):

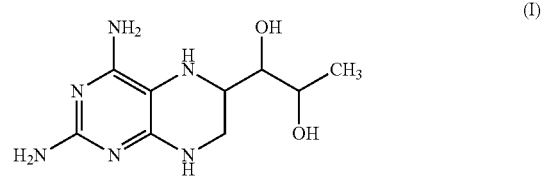 [SMILES: CC(O)C(O)C1CNc2nc(N)nc(N)c2N1]

(I)

and/or a compound having the formula (II):

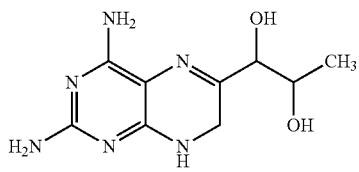

and b) at least one phosphate salt and optionally NaCl;
the method comprising:

aa) dissolving a compound of the formula (III) and/or the compound of the formula (II):

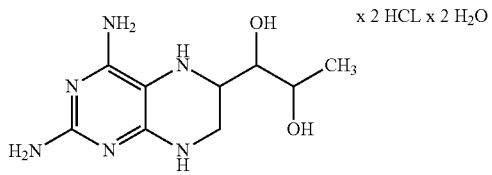

with a buffer, wherein preferably the buffer comprises the phosphate;

bb) lyophilization of the solution obtained in aa).

In some embodiments, the method of the present invention further comprises the step of dissolving the lyophilisate obtained in bb) in a pharmaceutically acceptable fluid for the preparation of an injectable solution.

Accordingly, the present invention also relates to a method for preparing an injectable solution comprising:

a) a compound having the formula (I):

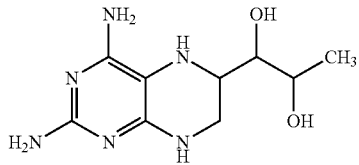

and/or a compound having the formula (II):

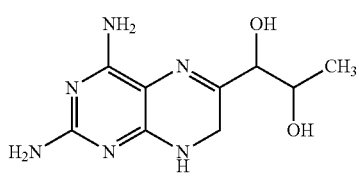

and b) at least one phosphate salt and optionally NaCl;
the method comprising:

aa) dissolving the compound of the formula (III) and/or (II):

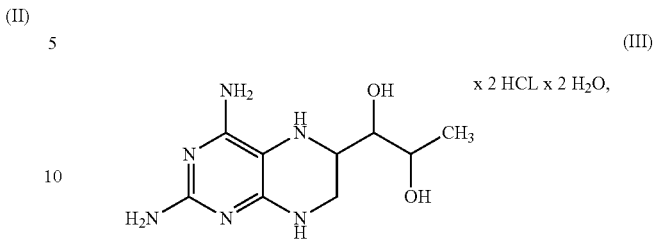

with a buffer, wherein preferably the buffer comprises the phosphate;

bb) lyophilization of the solution obtained in aa);

cc) reconstituting the lyophilisate obtained in bb) in a pharmaceutically acceptable fluid for the preparation of an injectable solution, wherein the lyophilisate obtained in bb) is filled into a vial.

In one embodiment of the method of the present invention the lyophilisate obtained in bb) is filled into a 50 ml vial,
  (i) preferably in an amount about 1-1.5 g, preferably 1.25 g solid formulation; or
  (ii) preferably in an amount about 0.9-1.4 g, preferably 1.15 g solid formulation.

In other embodiments in the method of the present invention the buffer in aa) is a sodium hydrogen phosphate buffer comprising at least one phosphate salt.

In other embodiments in the method of the present invention the buffer in aa) comprises NaOH, sodium hydrogen phosphate buffer and water. Optionally, the NaOH is a 5 N NaOH dissolution.

In another embodiment of the method of the present invention the sodium hydrogen phosphate buffer is prepared by separately dissolving $NaH_2PO_4.2H_2O$ and $Na_2HPO_4.2H_2O$.

In a further embodiment of the method of the present invention the sodium hydrogen phosphate buffer has a pH of 7.4 by adding the $NaH_2PO_4.2H_2O$ dissolution to the $Na_2HPO_4.2H_2O$ dissolution.

In some embodiments of the method of the present invention the buffer comprises 12-16% (w/w) NaOH 5N, 8-12% (w/w) sodium hydrogen phosphate buffer and 74-78% (w/w) water for injection.

In another embodiment of the method of the present invention, the solution obtained in aa) is sterile filtered, preferably with a 0.22 μm filter.

In further embodiments of the method of the present invention, the buffer has a pH of about 8, 9, 10, 11, 12, 13 or 14.

In yet another embodiment of the method of the present invention, the solution in step aa) has a pH of about 4, 5, 6, 7, 8, 9, 10 or 11 preferably between 6.5-7.6, most preferably 7.4.

In other embodiments of the method of the present invention, the lyophilisate obtained in bb) is filled into vials, preferably in an amount about 1-1.5 g, preferably 1.25 g solid formulation; or preferably in an amount about 0.9-1.4 g, preferably 1.15 g solid formulation.

In further embodiments of the method of the present invention the buffer is prepared with degassed buffer. In some embodiments, the buffer is degassed with nitrogen until the oxygen content is <1.0 ppm.

In another embodiment of the method of the present invention after the preparation of the solution; the lyophilisation is started at most 2 hours later.

The present invention also relates to a pharmaceutical composition obtainable by the method of the present invention.

The present invention further relates to the use of the lyophilized pharmaceutical composition of the present invention in the manufacture of a medicament for treating a subject having traumatic brain injury such as closed head injury, elevated cranial pressure but also secondary brain injury or non-traumatic brain injury such as stroke or meningitis.

Also, the present invention relates to a method of treating a disease in a subject, comprising the step of administering a lyophilized pharmaceutical composition of the present invention to a subject in need thereof. In some embodiments, in the method of treating a disease in a subject the maximal daily dose is 20 mg/kg body weight and day, preferably, 17.5, 15.0, or 12.5, 10, 8.5, 7.5, 5.0, or 2.5 mg/kg body weight and day.

The present invention also relates to a lyophilized pharmaceutical composition for use in treating a disease in a subject, the use comprising the step of administering a lyophilized pharmaceutical composition of the present invention to a subject in need thereof. In some embodiments, the maximal daily dose is 20 mg/kg body weight and day, preferably, 17.5, 15.0, or 12.5, 10, 8.5, 7.5, 5.0, or 2.5 mg/kg body weight and day.

In yet another embodiment the invention relates to a solid pharmaceutical composition (adapted for intravenous administration) comprising a) a compound having the formula (I):

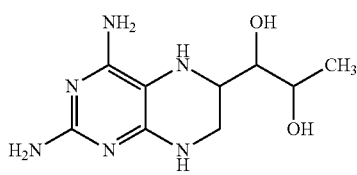

(I)

and/or a compound having the formula (II):

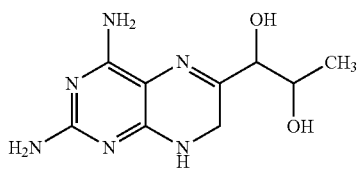

(II)

and b) at least one inorganic salt, preferably NaCl.

In such an embodiment, the quantity of the NaCl present in the composition of the present invention may be chosen such that the molar ratio of the NaCl to compound (I) or compound (II) ranges from 1.5 to 4, preferably from 1.8 to 3.7, from 1.85 to 3.6, from 1.9 to 3.4, most preferably from 1.9 to 2.5.

In one embodiment the molar ratio of NaCl to compound (I) or compound (II) is about 2.2.

BRIEF DESCRIPTION OF THE DRAWINGS

FIG. 3 shows the stability of 1 g VAS203 vials (batch no. 928606), stored at 2-8° C. (Table 5).

DETAILED DESCRIPTION OF THE INVENTION

Figure 1:
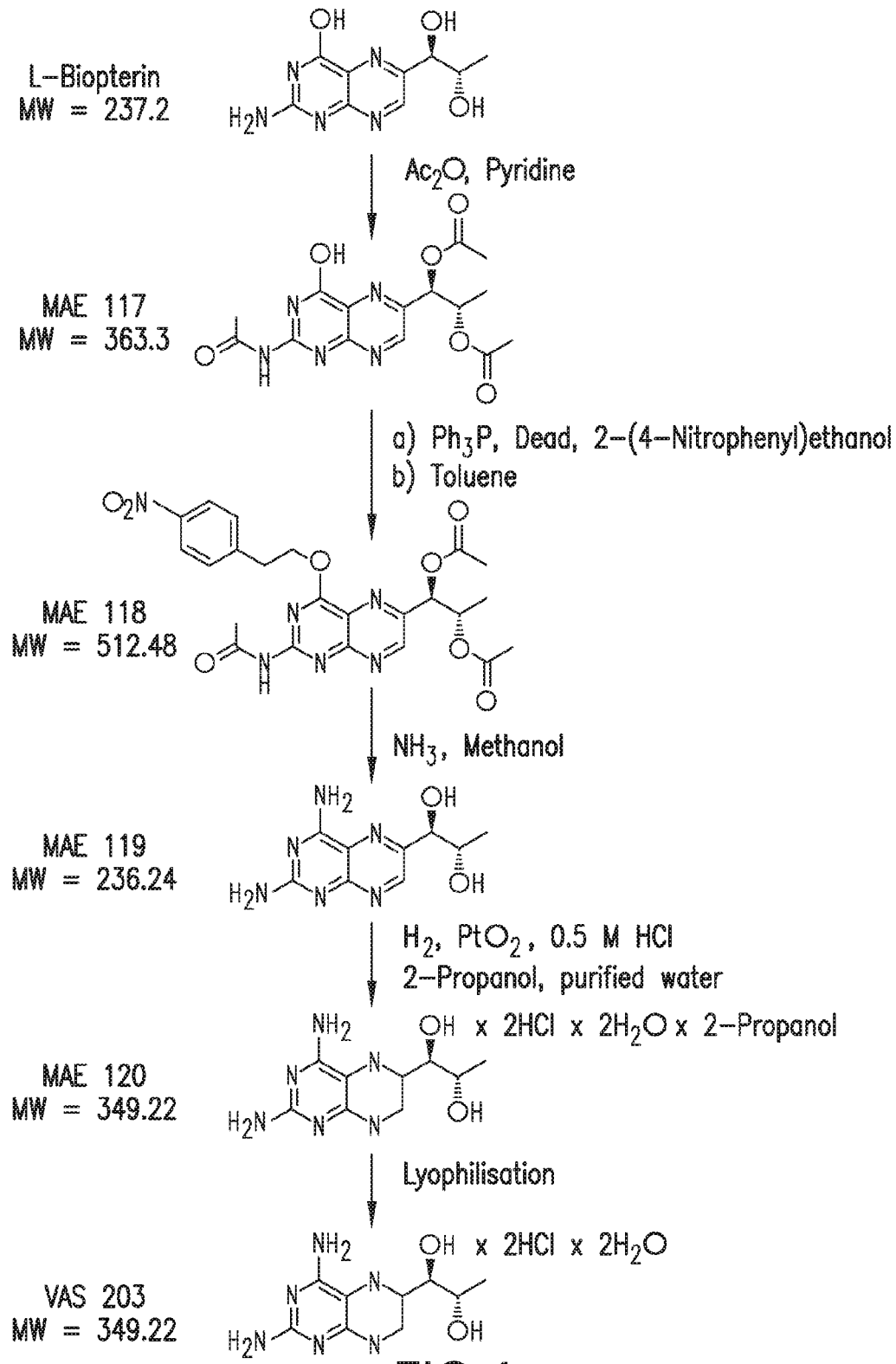
FIG. 1 shows the preparation of 4-Amino-(6R,S)-5,6,7,8-tetrahydro-L-biopterin dihydrochloride dihydrate (VAS203) drug substance.

It was an object of the present invention to provide pharmaceutical compositions. Additionally, these compositions should be easy to use and stable. It has been found herein that by using solid phosphate salts (alone or in connection with an inorganic salt such as NaCl or KCl) in connection with solid biopterin derivatives such as the compounds of formula (I) or (II) results in pharmaceutical compositions (formulations) that are very well adapted to achieve a pH value or pH range as well as an osmolality that, upon dissolution, is directly suitable for therapeutic administration. The solid pharmaceutical compositions are particularly well suited and easy to use, since they are already adapted for intravenous administration, thereby also ensuring save usage. In addition, the problem of oxidation of biopterin derivatives in liquids is being solved by the provision of solid compositions.

Thus, the present invention relates to a solid pharmaceutical composition (adapted for intravenous administration) comprising a) a compound having the formula (I):

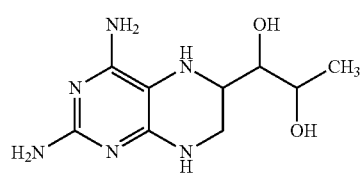

(I)

and/or a compound having the formula (II):

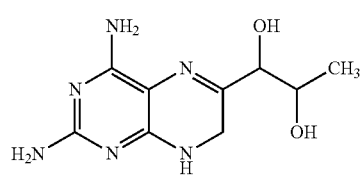

(II)

and b) at least one phosphate salt.

In addition, the present invention also relates to a solid pharmaceutical composition (adapted for intravenous administration) comprising a) a compound having the formula (I):

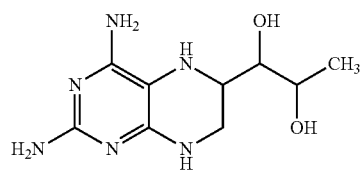

(I)

and/or a compound having the formula (II):

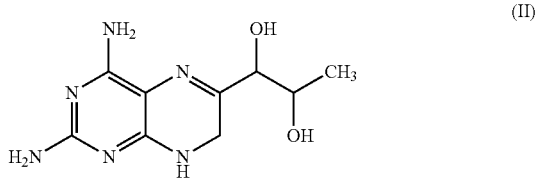 [SMILES: CC(O)C(O)C1=Nc2c(N)nc(N)nc2NC1]

(II)

and
b) at least one inorganic salt, in particular NaCl.

The term "solid" or "solid composition" when used herein relates to particles (ions, atoms or molecules or compounds) which are closely packed together. The forces between particles are strong so that the particles cannot move freely but can only vibrate. As a result, a solid has a stable, definite shape, and a definite volume. Solids can only change their shape by force, as when broken or cut. In crystalline solids, the particles (atoms, molecules, or ions) are packed in a regularly ordered, repeating pattern. There are various different crystal structures, and the same substance can have more than one structure (or solid phase). The term "solid" also encompasses amorphous or non-crystalline compositions/substances/solids. Usually, the aggregate state is determined at room temperature and ambient pressure. Room temperature commonly represents the small range of temperatures at which the air feels neither hot nor cold, often denoted is the range between 20 and 23.5° C. with an average of 21° C. (70° F.). With ambient pressure is meant a pressure between 900 and 1200 hPa (hekto Pascal), preferably about 1000 hPa. Solids can be transformed into liquids by melting, and liquids can be transformed into solids by freezing. Solids can also change directly into gases through the process of sublimation.

The solid composition of the present invention can be administered (usually upon dissolution in a liquid such as water) to an individual ("administration"). This provides administration of a therapeutically effective dose of the solid composition of the present invention to a subject.

The "therapeutically effective amount" is a dose of the compound of formula (I) and/or the compound of formula (II) that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art. In this context, it is noted again that both compounds, 4-Amino-5,6,7,8-tetrahydro-L-biopterin and 4-Amino-7,8-dihydro-L-biopterin are pharmaceutically active. It is also noted that 4-Amino-7,8-dihydro-L-biopterin can be obtained by oxidation (also spontaneous oxidation) from 4-Amino-5,6,7,8-tetrahydro-L-biopterin. Thus, a composition of the invention can comprise either only 4-Amino-5,6,7,8-tetrahydro-L-biopterin or 4-Amino-7,8-dihydro-L-biopterin or mixture of these two compounds in any ratio.

The solid compositions of the present invention are applicable to both human therapy and veterinary applications. The compounds described herein having the desired therapeutic activity may be administered in a pharmaceutically acceptable carrier to a patient/subject, as described herein. Depending upon the manner of introduction, the compounds may be formulated in a variety of ways as discussed below.

The solid composition of the present invention maybe administered alone or in combination with other treatments.

The solid composition of the present invention may be further "adapted for intravenous administration". This means that, after the solid composition is preferably mixed with a pharmaceutically acceptable carrier, preferably a pharmaceutically acceptable fluid, e.g. water or buffer or any of the reconstitution fluid as described below, a composition is obtained which directly as such can be used for intravenous application. Thus, after the mixing of the solid composition with the pharmaceutically acceptable carrier a ready-to-use composition, which is suitable for intravenous application, is obtained. Intravenous administration is the infusion or injection of liquid substances directly into a vein usually with a syringe and a hollow needle which is pierced through the skin to a sufficient depth for the material to be administered into the body of the subject.

Thus, in further embodiments the pharmaceutical composition of the present invention is adapted for administration by infusion or injection. With an "infusion" is meant a continuous administration over a certain period of time. For example such an administration may take in between 10 minutes to 4 days. Thus it can take at most 1, 2, 3, 4, 5, 6, 7, 8, 9, 10, 11, 12, 13, 14, 15, 16, 17, 18, 19, 20, 21, 22, 23, 24, 32, 40, 48, 56, 68, 72, 86, or 96 hours. An "injection" means is a transient infusion method of putting fluid into the body of a subject. Usually such an administration takes less than 10 minutes. However, an injection can be repeated various times a day. For example, an injection may take place 1, 2, 3, 4, 5, 6, 7, 8 or 9 times a day. Further the injection(s) may be administered for 1, 2, 3 or 4 days. However, the administration via injection or infusion can also take longer if needed. It is clear that the exact duration depends on many factors.

Typically, compositions for intravenous administration are the solid pharmaceutical composition of the present invention mixed with a pharmaceutically acceptable carrier, for example, with sterile isotonic aqueous buffer to form a pharmaceutical solution. Where necessary, this composition/solution may also include a solubilizing agent and a local anaesthetic such as lignocaine to ease pain at the site of the injection. Generally, the ingredients are supplied either separately or mixed together in unit dosage form, for example, as a dry lyophilised powder or water free concentrate in a hermetically sealed container such as a vial, an ampoule or sachette indicating the quantity of compound (I) and/or compound (II). Where the composition/solution is to be administered by infusion, it can be dispensed with an infusion bottle containing sterile pharmaceutical grade water or saline. Where the composition is administered by injection or infusion, an ampoule of sterile water for injection or saline can be provided so that the ingredients may be mixed prior to administration.

The term "pharmaceutically acceptable" means approved by a regulatory agency or other generally recognized pharmacopoeia for use in animals, and more particularly in humans. Generally "pharmaceutically acceptable" means also "physiologically acceptable" which means that the fluid/carrier is in accord with or characteristic of the normal functioning of a living subject and does not provoke toxicity or any other adverse effects. Such a fluid/carrier normally has about the same pH and/or osmolality as e.g. fluids such as the blood of an animal.

The "pharmaceutically acceptable fluid" can be one of the following non-limiting list of non-aqueous or aqueous solvents. Non-aqueous solvents are propylene glycol, polyethylene glycol, vegetable oils such as olive oil, and injectable organic esters such as ethyl oleate. Aqueous solvents include water, alcoholic/aqueous solutions, emulsions or suspensions, including saline and buffered media, sodium ion solution, Ringer's dextrose, dextrose and sodium ion, lactated Ringer's, or fixed oils. Intravenous vehicles include fluid and nutrient replenishers, electrolyte replenishers (such as those based on Ringer's dextrose), and the like. A preferred pharmaceutically acceptable fluid is an aqueous solvent for example sterile water for injection.

In some embodiments, the solid pharmaceutical composition of the present invention is reconstituted before administration. In other embodiments, the pharmaceutical composition of the present invention is adapted to be reconstituted in water. "Reconstituted in water" means to return (a dehydrated or concentrated) composition to the liquid state by adding a pharmaceutically acceptable fluid as described above. Preferably, the solid composition of the present invention is reconstituted in water. \

The invention may comprise different solid compositions. For example, the solid composition can comprise compound (I) and/or compound (II) in addition to a phosphate salt. By a "phosphate salt" is meant that any known phosphate salt can be used. Phosphate salts refer to many different combinations of the chemical phosphate with salts and minerals. In one embodiment in the pharmaceutical composition of the present invention, the at least one phosphate salt is a sodium phosphate, a potassium phosphate or an ammonium phosphate. The phosphate salt can be selected from the group consisting of $Na_2HPO_4$ (water free), $Na_2HPO_4.2H_2O$, $Na_2HPO_4.7H_2O$, $Na_2HPO_4.12H_2O$, $NaH_2PO_4$ (water free), $NaH_2PO_4.H_2O$, $NaH_2PO_4.2H_2O$, $K_2HPO_4$ (water free) $K_2HPO_4.3H_2O$, $KH_2PO_4$ (water free) and mixtures thereof.

In some embodiments of the pharmaceutical composition of the present invention, the phosphate salt is $Na_2HPO_4.2H_2O$ and the quantity of the $Na_2HPO_4.2H_2O$ present in the composition is chosen such that the molar ratio of the $Na_2HPO_4.2H_2O$ to compound (I) or compound (II) ranges from 0.04 to 0.4, preferably from 0.05 to 0.35, from 0.075 to 0.25, from 0.09 to 0.2. In one embodiment the molar ratio of the $Na_2HPO_4.2H_2O$ to compound (I) or compound (II) is about 0.144.

In further embodiments of the pharmaceutical composition of the present invention, the sodium phosphate is $NaH_2PO_4.2H_2O$, and the quantity of the $NaH_2PO_4.2H_2O$ present in the composition is chosen such that the molar ratio of the $NaH_2PO_4.2H_2O$ to compound (I) or compound (II) ranges from 0.01 to 0.09 preferably from 0.015 to 0.07, from 0.02 to 0.05, from 0.025 to 0.04, from 0.035 to 0.05. In one embodiment the molar ratio of the $NaH_2PO_4.2H_2O$ to compound (I) or compound (II) is about 0.038.

In other embodiments, the pharmaceutical composition of the present invention comprises two different sodium phosphate salts. Optionally, the two different sodium phosphate salts are $NaH_2PO_4.2H_2O$ and $Na_2HPO_4.2H_2O$.

In some embodiments of the pharmaceutical composition of the present invention, the quantity of the $NaH_2PO_4.2H_2O$ and $Na_2HPO_4.2H_2O$ present in the composition is chosen such that the molar ratio of both $NaH_2PO_4.2H_2O$ and $Na_2HPO_4.2H_2O$ to compound (I) or compound (II) ranges from 0.02 to 0.5, preferably from 0.03 to 0.45, from 0.04 to 0.3, from 0.05 to 0.25, from 0.06 to 0.2, from 0.07 to 0.15. In one embodiment the molar ratio of both $NaH_2PO_4.2H_2O$ and $Na_2HPO_4.2H_2O$ to compound (I) or compound (II) is about 0.18.

In some embodiments of the pharmaceutical composition of the present invention, the quantity of the $NaH_2PO_4.2H_2O$ and $Na_2HPO_4.2H_2O$ present in the composition is chosen such that the molar ratio of each of $NaH_2PO_4.2H_2O$ and $Na_2HPO_4.2H_2O$ to compound (I) or compound (II) ranges from 0.02 to 0.5, preferably from 0.025 to 0.4, from 0.025 to 0.3, from 0.025 to 0.2, from 0.03 to 0.1. In some embodiments the quantity of the $NaH_2PO_4.2H_2O$ present in the composition is chosen such that the molar ratio of the $NaH_2PO_4.2H_2O$ to compound (I) or compound (II) ranges from 0.01 to 0.09 and the quantity of the $Na_2HPO_4.2H_2O$ present in the composition is chosen such that the molar ratio of the $Na_2HPO_4.2H_2O$ to compound (I) or compound (II) ranges from 0.04 to 0.4. Here, also the other quantities of the singly applied phosphate salts $Na_2HPO_4.2H_2O$ and $NaH_2PO_4.2H_2O$ as described above apply. In some embodiments, the solid pharmaceutical composition comprises least 1, 2, 3, 4, 5, 6, or more phosphate salts. In one embodiment the solid pharmaceutical composition of the present invention comprises 2 (different) phosphate salts.

When used herein, the term "about" is understood to mean that there can be variation in the respective value or range (such as pH, concentration, percentage, molarity, time etc.) that can be up to 5%, up to 10%, up to 15% or up to and including 20% of the given value. For example, if a formulation comprises about 5 mg/ml of a compound, this is understood to mean that a formulation can have between 4 and 6 mg/ml, preferably between 4.25 and 5.75 mg/ml, more preferably between 4.5 and 5.5 mg/ml and even more preferably between 4.75 and 5.25 mg/ml, with the most preferred being 5 mg/ml. The same applies also to molarity. For example a molarity of about 1 is to be understood as a molarity of between 0.8 to 1.2, preferably 0.85 to 1.15, more preferably between 0.9 to 1.1, even more preferably between 0.95 to 1.05 with the most preferred being 1.

Alternatively, the present invention relates to solid compositions, which comprise compound (I) and/or compound (II) and an inorganic salt different from a phosphate salt. In these compositions, the inorganic salt can either be the sole components apart from compound (I) or (II) (in this case, there is no phosphate salt present). Alternatively, in composition of the invention an inorganic salt can be present in combination with at least one phosphate. The term "inorganic salt" when referred to herein means every suitable inorganic salt. Optionally, the inorganic salt is selected from $MgCl_2$, $CaCl_2$, $NH_4Cl$, KCl, or NaCl. In some preferred embodiments the inorganic salt is NaCl. In some embodiments of the pharmaceutical composition of the present invention the quantity of the NaCl present in the composition of the present invention (alone or together with at least one phosphate) is chosen such that the molar ratio of the NaCl to compound (I) or compound (II) ranges from 1.5 to 4, preferably from 1.8 to 3.7, from 1.85 to 3.6, from 1.9 to 3.4, most preferably from 1.9 to 2.5. In one of such embodiments the molar ratio of the NaCl to compound (I) or compound (II) is about 2.2

In the compositions of the invention, compounds (I) and/or compound (II) can be present as diastereomeric mixtures or mixtures of 1, 2, 3, 4, 5, 6, 7 or 8 stereoisomers for compound (I) and 1, 2, 3, 4, 5 or 6 stereoisomers for compound (II), preferably of one or two stereoisomers.

The compound of formula (I) can thus comprise diastereomeric mixtures of compound of formula (I) or mixtures of one or more stereoisomers of the compound of formula (I). The compound (I) can be (6R)-4-Amino-5,6,7,8-tetrahydro-L-biopterin. In further embodiments the compound (I) is (6S)-4-Amino-5,6,7,8-tetrahydro-L-biopterin. In other embodiments the compound (I) is a diastereomeric mixture that comprises more (6R)-4-Amino-5,6,7,8-tetrahydro-L-biopterin than (6S)-4-Amino-5,6,7,8-tetrahydro-L-biopterin. In some embodiments the quantity of the (6R)-4-Amino-5,6,7,8-tetrahydro-L-biopterin and the (6S)-4-Amino-5,6,7,8-tetrahydro-L-biopterin is chosen such that the ratio of the amount of (6R)-4-Amino-5,6,7,8-tetrahydro-L-biopterin to the (6S)-4-Amino-5,6,7,8-tetrahydro-L-biopterin ranges from 0.5 to 2, preferably from 0.5 to 1.9, from 0.7 to 1.8, from 0.8 to 1.7, from 0.9 to 1.6, from 1 to 1.5, most preferably from 1.1 to 1.4. In one embodiment, the quantity of the (6R)-4-Amino-5,6,7,8-tetrahydro-L-biopterin and the (6S)-4-Amino-5,6,7,8-tetrahydro-L-biopterin is chosen such that the ratio of the amount of (6R)-4-Amino-5,6,7,8-tetrahydro-L-biopterin to the (6S)-4-Amino-5,6,7,8-tetrahydro-L-biopterin is around 1.3. In some embodiments, the pharmaceutical composition of the present invention comprises only compound (I).

The compound (I) can also be a compound having the formula (Ia):

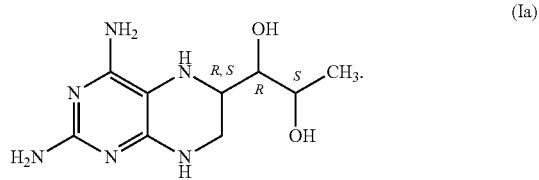

Similarly, the compound of formula (II) when referred to herein can comprise stereoisomeric mixtures of compound of formula (II) or mixtures of one or more stereoisomer of the compound of formula (II). In some embodiments of the pharmaceutical composition of the present invention the compound (II) is 4-Amino-7,8-dihydro-L-biopterin. In another embodiment, the compound (II) is a compound having the formula (IIa):

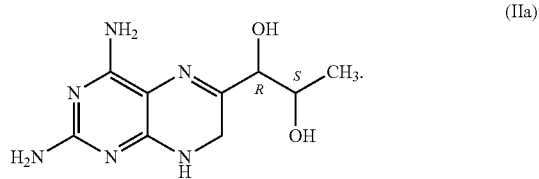

In some embodiments, the pharmaceutical composition of the present invention comprises only compound (II).

Within the solid pharmaceutical compositions compound (I) and/or the compound (II) can also be present as the free base. A "free base" when referred to herein refers to the pure basic form of an amine, as opposed to its salt form. Further, this term is used to describe the deprotonated amine form of a compound. A common counter ion is an ion from an inorganic acid such as a negatively charged chloride. For example, compare the free base amine ($NH_2$) with amine hydrochloride ($NH_3^+Cl^-$) when adding HCl.

As mentioned above, the biopterin derivatives are sensitive against oxidation in liquids. Therefore, the solid pharmaceutical composition can also be provided as a lyophilized pharmaceutical composition. The term "lyophilized" when used herein means freeze-drying, which is a dehydration process. Freeze-drying works by freezing the material and then reducing the surrounding pressure to allow the frozen water in the material to sublimate directly from the solid phase to the gas phase. In some embodiments the final residual water content in the lyophilized product is between 0% to 15%, preferably between 0% to 12%, (w/w).

Methods to perform lyophilisation are known to the person skilled in the art.

As evident for the person skilled in the art, the pharmaceutical compositions can further comprise 1, 2, 3, 4, 5, 6, 7, 8, 9, 10 or more additional pharmaceutical excipients. A "pharmaceutical excipient" or additives are compounds added to the compounds of the formula (I) and/or (II). These additives might serve a specific function. They may be added to increase bulk, aid manufacturing, improve stability, enhance drug delivery and targeting, and modify drug safety or pharmacokinetic profile. Ingredients that are used during drug product manufacturing but may not be present in the solid composition of the present invention are also considered excipients (examples include water for lyophilized products, and inert gases in the head space of containers). Suitable pharmaceutical excipients include starch, glucose, lactose, sucrose, trehalose, mannitol, sorbitol, glycine, histidine, raffinose, gelatine, malt, rice, flour, chalk, silica gel, sodium stearate, glycerol monostearate, talc, sodium ion, dried skim milk, glycerol, propylene, glycol, dextrose, dextran, water, ethanol and the like. The composition, if desired, can also contain minor amounts of wetting or emulsifying agents, or pH buffering agents. These compositions can take the form of solutions, suspensions, emulsion and the like.

If, for example, the solid composition of the present invention comprises a compound of formula (I) and/or of formula (II) and a phosphate salt, a possible additional pharmaceutical excipient can be an inorganic salt. The inorganic salt can be any inorganic salt as described above. On the other hand, if the pharmaceutical composition of the present invention, comprises a compound of formula (I) and/or of formula (II) and a inorganic salt, an additional pharmaceutical excipient can be a phosphate salt. The phosphate salt can be any phosphate salt as described above.

In addition to the pharmaceutical excipients which may be present in the solid pharmaceutical compositions of the present inventions, in some embodiments the pharmaceutical composition of the present invention can comprise crystallization water, of course an additional pharmaceutical excipients can also be present as well. As used herein in accordance with its regular meaning in the art, "water of crystallization" or "water of hydration" or "crystallization water" means water that occurs inside crystals—in the present invention, both the inorganic salts such as $Na_2HPO_4$ or $NaH_2PO_4$ as well as the biopterin derivate of compound (I) or compound (II) can have water of crystallization. While in the solid phosphate salts such as $Na_2HPO_4.2H_2O$, or $NaH_2PO_4.2H_2O$ the water of crystallization is present in defined stoichiometric amounts, the amount of water of crystallization present in the solid form of compound (I) or compound (II) may vary depending on the conditions for the synthesis and/or crystallization of the compound that is used for the preparation of the solid formulation of the present invention. Without wishing to be bound by theory, it is believed that the water of crystallization that is present in the solid form of compound (I) or compound (II) can, for example, be bound via hydrogen bonds to the two amino groups of compound (I) or (II) which are present as free base. For illustrative purposes, it referred in this context to a unit dosage of the composition that contains 650±60 mg of the free base of 4-Amino-(6R,S)-5,6,7,8-tetrahydro-L-biopterin, 140±30 mg of water of crystallization, 70±7 mg $Na_2HPO_4.2H_2O$, 16.5±2 mg $NaH_2PO_4.2H_2O$, and 350±30 mg sodium chloride (NaCl). In this unit dosage the two sodium phosphate salts are present as dihydrates, while the crystallization water that is present in the amount of 140±30 mg of water of crystallization only refers to the water that present in association with the free base of compound (I) and/or compound (II). Another exemplary unit dosage of the composition contains 650±60 mg of the free base of 4-Amino-(6R,S)-5,6,7,8-tetrahydro-L-biopterin, 60±50 mg of water of crystallization, 70±7 mg $Na_2HPO_4.2H_2O$, 12±2.5 mg $NaH_2PO_4.2H_2O$, and 350±30 mg sodium chloride (NaCl).

As just described, the pharmaceutical composition of the present invention may be provided in a unit dosage. A "unit dosage" of the solid pharmaceutical compositions of the present invention means that the ingredients are mixed together in a unit dosage, typically involving a mixture of active drug components such as compound (I) and/or compound (II) and nondrug components (excipients) such as at least one phosphate salt and/or at least one inorganic salt. Additionally, a unit dosage may comprise further excipients such as at least one phosphate salt or at least one inorganic salt and/or along other non-reusable material that may not be considered either ingredient or packaging (such as a capsule shell, for example). The term unit dosage can also encompass non-reusable packaging as well (especially when each drug product is individually packaged). The unit dosage can also comprise reconstituted solid pharmaceutical compositions of the present inventions.

For an exemplary unit dosage in the following a calculation of the molar ratios of the ingredients in this unit dosage is outlined in Table 1.

TABLE 1

| | Composition | Molar mass | Mol (mean) | form |
|---|---|---|---|---|
| $C_9H_{16}N_6O_2$ | Compound of formula (i) | 650 +/− 60 mg | 240.27 g/mol | 0._0027053 | solid |
| $C_9H_{14}N_6O_2$ | Compound of formula (ii) | 650 +/− 60 mg | 238.26 g/mol | 0.0027282 | solid |
| $H_2O$ | Water of crystallization | 140 +/− 30 mg | 18.02 g/mol | 0.0077691 | |
| NaCl | Sodium chloride | 350 +/− 30 mg | 58.44 g mol−1 | 0.005989 | salt |
| $Na_2HPO_4 \cdot 2H_2O$ | Disodium hydrogen phosphate Dihydrate | 70 +/− 7 mg | 177.99 g/mol | 0.0003932 | Dihydrate solid |
| $NaH_2PO_4 \cdot 2H_2O$ | Sodium dihydrogen phosphate Dihydrate | 16.5 +/− 2 mg | 156.01 g/mol | 0.0001057 | Dihydrate solid |

Molar ratio between $n_{NaCl}/n_{compound\ (i)}$=0.005989 mol/0.0027053 mol~2.214

Molar ratio between $n_{NaCl}/n_{compound\ (ii)}$=0.005989 mol/0.0027282 mol~2.195

Molar ratio between $n_{Na2HPO4.2H2O}+n_{NaH2PO4.2H2O}/n_{compound\ (i)}$=0.0003932 mol+0.0001057 mol/0.0027053 mol~0.18

Molar ratio between $n_{Na2HPO4.2H2O}+n_{NaH2PO4.2H2O}/n_{compound\ (ii)}$=0.0003932 mol+0.0001057 mol/0.0027282 mol~0.18

Molar ratio between $n_{Na2HPO4.2H2O}/n_{compound\ (i)}$=0.0003932 mol/0.0027053 mol~0.145

Molar ratio between $n_{Na2HPO4.2H2O}/n_{compound\ (ii)}$=0.0003932 mol/0.0027282 mol~0.144

Molar ratio between $n_{NaH2PO4.2H2O}/n_{compound\ (i)}$=0.0001057 mol/0.0027053 mol~0.038

Molar ratio between $n_{NaH2PO4.2H2O}/n_{compound\ (ii)}$=0.0001057 mol/0.0027282 mol~0.038

$n_{compound\ (i)}=m_{compound\ (i)}/M_{compound\ (i)}$=0.710 g/240.27 g mol$^{-1}$=0.002955 mol $n_{compound\ (i)}=m_{compound\ (i)}/M_{compound\ (i)}$=0.590 g/240.27 g mol$^{-1}$=0.0024556 mol $n_{compound\ (i)}=m_{compound\ (i)}/M_{compound\ (i)}$=0.650 g/240.27 g mol$^{-1}$=0.0027053 mol $n_{compound\ (ii)}=m_{compound\ (ii)}/M_{compound\ (ii)}$=0.710 g/238.25 g mol$^{-1}$=0.00298 mol $n_{compound\ (ii)}=m_{compound\ (ii)}/M_{compound\ (ii)}$=0.590 g/238.25 g mol$^{-1}$=0.0024763 mol $n_{compound\ (ii)}=m_{compound\ (ii)}/M_{compound\ (ii)}$=0.650 g/238.25 g mol$^{-1}$=0.0027282 mol $n_{NaCl}=m_{NaCl}/M_{NaCl}$=0.380 g/58.44 g mol$^{-1}$=0.0065023 mol $n_{NaCl}=m_{NaCl}/M_{NaCl}$=0.320 g/58.44 g mol$^{-1}$=0.0054757 mol $n_{NaCl}=m_{NaCl}/M_{NaCl}$=0.350 g/58.44 g mol$^{-1}$=0.005989 mol $n_{Na2HPO4.2H2O}=m_{Na2HPO4.2H2O}/M_{Na2HPO4.2H2O}$=0.077 g/177.99 g mol$^{-1}$=0.0004326 mol $n_{Na2HPO4.2H2O}=m_{Na2HPO4.2H2O}/M_{Na2HPO4.2H2O}$=0.063 g/177.99 g mol$^{-1}$=0.0003539 mol $n_{Na2HPO4.2H2O}=m_{Na2HPO4.2H2O}/M_{Na2HPO4.2H2O}$=0.07 g/177.99 g mol$^{-1}$=0.0003932 mol $n_{NaH2PO4.2H2O}=m_{NaH2PO4.2H2O}/M_{NaH2PO4.2H2O}$=0.0185 g/156.01 g mol$^{-1}$=0.0001185 mol $n_{NaH2PO4.2H2O}=m_{NaH2PO4.2H2O}/M_{NaH2PO4.2H2O}$=0.0145 g/156.01 g mol$^{-1}$=0.0000929 mol $n_{NaH2PO4.2H2O}=m_{NaH2PO4.2H2O}/M_{NaH2PO4.2H2O}$=0.0165 g/156.01 g mol$^{-1}$=0.0001057 mol $n_{H2O}=m_{H2O}/M_{H2O}$=0.17 g/18.02 g mol$^{-1}$=0.0094339 mol $n_{H2O}=m_{H2O}/M_{H2O}$=0.11 g/18.02 g mol$^{-1}$=0.0061043 mol $n_{H2O}=m_{H2O}/M_{H2O}$=0.14 g/18.02 g mol$^{-1}$=0.0077691 mol In summary, a unit dosage as described herein may contain 650±60 mg of the free base of 4-Amino-7,8-dihydro-L-biopterin and/or of 4-Amino-(6R,S)-5,6,7,8-tetrahydro-L-biopterin, 140±30 mg of water of crystallization, 70±7 mg $Na_2HPO_4.2H_2O$, 16.5±2 mg $NaH_2PO_4.2H_2O$, and 350±30 mg NaCl. It is also possible that a unit dosage of the composition contains 650±60 mg of the free base of 4-Amino-(6R,S)-5,6,7,8-tetrahydro-L-biopterin, 60±50 mg of water of crystallization, 70±7 mg $Na_2HPO_4.2H_2O$, 12±2.5 mg $NaH_2PO_4.2H_2O$, and 350±30 mg sodium chloride (NaCl). In typical embodiments, this unit dosage refers to and is packaged for administration in a 50 ml vial since after reconstitution with a volume of 50 ml pharmaceutically acceptable carrier such as water ad inject an infusion or injection solution that can be immediately administered is obtained. Thus, if for example, a different unit dosage is used, for example a 30 ml vial, the amounts of all components of the composition are adjusted accordingly. In the example of a 30 ml vial, the amount of each component would be reduced to 3/5 (60%). That means, if a unit dosage in a 50 ml vial contains 650±60 mg of the free base of 4-Amino-7,8-dihydro-L-biopterin and/or of 4-Amino-(6R,S)-5,6,7,8-tetrahydro-L-biopterin, 140±30 mg of water of crystallization, 70±7 mg $Na_2HPO_4.2H_2O$, 16.5±2 mg $NaH_2PO_4.2H_2O$, and 350±30 mg NaCl, then a 30 ml unit dosage will contain 390±36 mg of the free base of 4-Amino-7,8-dihydro-L-biopterin and/or of 4-Amino-(6R,S)-5,6,7,8-tetrahydro-L-biopterin, 84±18 mg of water of crystallization, 42±4.2 mg $Na_2HPO_4.2H_2O$, 9.9±1.2 mg $NaH_2PO_4.2H_2O$, and 210±18 mg NaCl. Accordingly, if a unit dosage in a 50 ml vial contains 650±60 mg of the free base of 4-Amino-7,8-dihydro-L-biopterin and/or of 4-Amino-(6R,S)-5,6,7,8-tetrahydro-L-biopterin, 60±50 mg of water of crystallization, 70±7 mg $Na_2HPO_4.2H_2O$, 12±2.5 mg $NaH_2PO_4.2H_2O$, and 350±30 mg NaCl, then a 30 ml unit dosage will contain 390±36 mg of the free base of 4-Amino-7,8-dihydro-L-biopterin and/or of 4-Amino-(6R,S)-5,6,7,8-tetrahydro-L-biopterin, 36±18 mg of water of crystallization, 42±4.2 mg $Na_2HPO_4.2H_2O$, 7.2±1.2 mg $NaH_2PO_4.2H_2O$, and 210±18 mg NaCl.

The pharmaceutical composition of the present invention can also comprise further molecules, for example, related compounds generated during the production process of the pharmaceutical composition of the present invention. Thus, the pharmaceutical composition of the present invention can comprise 1, 2, 3, 4, 5, 6, 7, or more additional compounds. These additional compounds may be selected from one or more of the compounds including, but not limited to, of the group consisting of 4-Amino-7,8-dihydro-L-biopterin (which might be generated by spontaneous oxidation of 4-Amino-5,6,7,8-tetrahydro-L-biopterin, see above), 4-Amino-L-biopterin, (6R,S)-5,6,7,8-Tetrahydro-L-biopterin, 1-[(6R,S)-2,4-Diamino-5,6,7,8-tetrahydropteridin-6-yl]propanol, 1-[(6R,S)-2,4-Diamino-5,6,7,8-tetrahydropteridin-6-yl]propane, (1R,2S)-1-[(6R,S)-2-(Acetylamino)-4-amino-5,6,7,8-tetrahydropterin-6-yl]-1,2-diacetoxypropane, 2,4-Diamino-7,8-dihydropteridine, or 2,4-Diaminopteridine, to name a few illustrative compounds.

As outlined above, pteridine derivatives have been shown to exhibit properties different from that of other NO-inhibitors, making the compound potentially more suitable than "classical" arginine analogues. Thus, the present invention also relates to a use of a lyophilized pharmaceutical composition of the present invention for the treatment of a disease. In some embodiments, the disease is selected from the group consisting of a traumatic brain injury, non-traumatic brain injury, preferably stroke or meningitis, elevated cranial pressure, secondary brain injury.

The term "traumatic brain injury" or "brain trauma" occurs when an external force traumatically injures the brain. TBI can be classified based on severity, mechanism (closed or penetrating head injury), or other features (e.g., occurring in a specific location or over a widespread area). A traumatic brain injury can occur as a consequence of a focal impact upon the head, by a sudden acceleration/deceleration within the cranium or by a complex combination of both movement and sudden impact, as well as blast waves, or penetration by a projectile. The Glasgow Coma Scale (GCS), the most commonly used system for classifying TBI severity, grades a person's level of consciousness on a scale of 3-15 based on verbal, motor, and eye-opening reactions to stimuli. In general, it is agreed that a TBI with a GCS of 13 or above is mild, 9-12 is moderate, and 8 or below is severe. Similar systems exist for young children. From the diagnostic point of view, it is further distinguished between open and closed TBIs. An open TBI is considered to be an injury in which the cerebral meninges (Dura mater) is mechanically destroyed and the brain is in contact with the environment through this opening. Often, an open TBI is associated with the exit of liquor and brain tissue debris. In a closed TBI the skull or cranium remains intact, and the primary damage of the brain (trauma) is characterized by local lesions such as contusions or hematomas and/or diffuse cerebral tissue damage. The term "cranium" when referred to herein is the set of out of the neurocranium (braincase) and the viscerocranium (craniofacial) existing bony and cartilaginous head skeleton of vertebrates. "Intracranial" means within the cranium.

To the contrary, a "non-traumatic brain injury" does not involve external mechanical force to acquire a brain injury. Causes for non-traumatic brain injury may include lack of oxygen, glucose, or blood. Infections can cause encephalitis (brain swelling), meningitis (meningeal swelling), or cell toxicity as e.g. caused by fulminant hepatic failure, as can tumours or poisons. These infections can occur through stroke, heart attack, near-drowning, strangulation or a diabetic coma, poisoning or other chemical causes such as alcohol abuse or drug overdose, infections or tumours and degenerative conditions such as Alzheimer's disease and Parkinson's disease. An acute neurodegenerative disease is represented by "stroke", which refers to the loss of brain function due to disturbances in the blood supply to the brain, especially when it occurs quickly, and is often associated with cerebrovascular disease. This can occur following ischemia (lack of blood flow) caused by blockage (thrombosis, arterial embolism), or a haemorrhage of central nervous system (CNS), or intracranial blood-vessels. As a result, the affected area of the brain cannot function normally.

Another disease which can be treated is "meningitis", which is an acute inflammation of the membranes covering the brain and spinal cord, known collectively as the meninges. The inflammation may be caused by infection with viruses, bacteria, or other microorganisms, and less commonly by certain drugs.

In addition to the damage caused at the moment of injury, brain trauma (non-traumatic or traumatic brain injury) causes "secondary injury" or secondary brain injury", which refers to a variety of events that take place in the minutes and days following the injury. These processes, which include alterations in cerebral blood flow and the pressure within the skull, contribute substantially to the damage from the initial injury. Secondary injury events may include for example damage to the blood-brain barrier, release of factors that cause inflammation, free radical overload, excessive release of the neurotransmitter glutamate (excitotoxicity), influx of calcium and sodium ions into neurons, and dysfunction of mitochondria. Injured axons in the brain's white matter may separate from their cell bodies as a result of secondary injury, potentially killing those neurons. Other factors in secondary injury are changes in the blood flow to the brain; repeated transient disintegrity of the blood brain barrier; ischemia (insufficient blood flow); cerebral hypoxia (insufficient oxygen in the brain); cerebral oedema (swelling of the brain); and raised intracranial pressure (the pressure within the skull).

It can also be that the intracranial pressure may elevate due to swelling or a mass effect from a lesion, such as a haemorrhage. As a result, cerebral perfusion pressure (the pressure of blood flow in the brain) is reduced; ischemia results. When the pressure within the skull rises too high, it can cause brain death or herniation, in which parts of the brain are squeezed by structures in the skull. The term "intracranial pressure" (ICP) means the pressure inside the cranium and thus in the brain tissue and cerebrospinal fluid (CSF). The body has various mechanisms by which it keeps the ICP stable, with CSF pressures varying by about 1 mmHg in normal adults through shifts in production and absorption of CSF. ICP is measured in millimeters of mercury (mmHg) and, at rest, is normally 7-15 mmHg for a supine adult. Changes in ICP are attributed to volume changes in one or more of the compartments contained in the cranium. An "elevated pressure in the cranium" or "elevated intracranial pressure" means an increased pressure in the cranium of a subject in comparison to a normal, healthy subject. As the intracranial pressure is normally between 7-15 mm Hg; thus at 20-25 mm Hg, the upper limit of normal, is already considered an elevated intracranial pressure and a treatment to reduce this pressure may be needed. Thus, as an elevated intracranial pressure can be considered any pressure higher that 20 mm Hg in the cranium of a supine subject, preferably a pressure is higher than 25 mm Hg, higher than 26 mm Hg, higher than 27 mm Hg, higher than 28 mm Hg, higher than 29 mm Hg, higher than 30 mm Hg, higher than 31 mm Hg, higher than 32 mm Hg, higher than 33 mm Hg, higher than 34 mm Hg or higher than 35 mm Hg.

Along this line, the present invention further relates to the use of the lyophilized pharmaceutical composition of the present invention in the manufacture of a medicament for treating a subject having closed head injury, elevated cranial pressure and secondary brain injury. A "closed head injury" when referred to herein means is a type of traumatic brain injury in which the cranium and dura mater remain intact (see also above).

Also, the present invention relates to a method of treating a disease in a subject, comprising the step of administering a lyophilized pharmaceutical composition of the present invention to a subject in need thereof.

For the administration, the attending physician and clinical factors will determine the dosage regimen. As is well known in the medical arts, dosages for any one patient depends upon many factors, including the patient's size, body surface area, age, the particular compound to be administered, sex, time and route of administration, general health, and other drugs being administered concurrently. A typical daily dose can be, for example, in the range of 2.5 mg/kg to 12.5 mg/kg body weight; however, doses below or above this exemplary range are also envisioned, especially considering the aforementioned factors.

The dosages are preferably given once a day for maximally 4 days, however, during progression of the treatment the dosages can be given in much longer time intervals and in need can be given in much shorter time intervals, e.g., daily. In a preferred case the immune response is monitored using herein described methods and further methods known to those skilled in the art and dosages are optimized, e.g., in time, amount and/or composition. Dosages will vary but a preferred dosage for intravenous administration of compound (I) and/or compound (II) is from approximately 2.5 mg/kg to 12.5 mg/kg body weight and day.

If the regimen is an injection or a continuous short-term infusion, it should also be in the range of about 1 µg to about 1 mg units per kilogram of body weight per minute, respectively. Progress can be monitored by periodic assessment.

In vitro assays may optionally be employed to help identify optimal dosage ranges. The precise dose to be employed in the formulation will also depend on the route of administration, and the seriousness of the disease, and should be decided according to the judgment of the practitioner and each patient's circumstances. Effective doses may be extrapolated from dose-response curves derived from in vitro or animal model test systems. Preferably, the pharmaceutical composition is administered directly or in combination with an adjuvant.

The maximal daily dose (DDD) is based on the amount of the compound (I) and/or (II), which typically is used for the main indication of subjects (e.g. adults) per day. However, the dosage regimen may differ from injections to infusions or even multiple injections and/or infusions a day. In some embodiments, in the method of treating a disease in a subject the maximal daily dose is 12.5 mg/kg body weight, preferably 12.5, 11.5, 10.5, 9.5 8.5, 7.5, 6.5, 5.5, 4.5, 3.5, 2.5 mg/kg body weight. In some embodiments, the maximal daily dose is 10.0, 9.0 or preferably 8.5 mg/kg body weight, or even lower such as 7.5, 5.0, 2.5 mg/kg body weight.

As used herein, an interval which is defined as "(from) X to Y" equates with an interval which is defined as "between X and Y". Both intervals specifically include the upper limit and also the lower limit. This means that for example an interval of "2.5 mg/kg to 12.5 mg/kg" or "between 2.5 mg/kg to 12.5 mg/kg" includes a concentration of 2.5, 3.5, 4.5, 5.5, 6.5, 7.5, 8.5, 9.5, 10.5, 11.5 and 12.5 as well as any given intermediate value.

It is also envisaged that the pharmaceutical compositions are employed in co-therapy approaches, i.e. in co-administration with other medicaments or drugs, for example other drugs for preventing, treating or ameliorating diseases such as traumatic or non-traumatic brain injury.

"Subjects" that are treated in the present invention are preferably mammals such as humans, monkeys, cats, dogs, horses, pigs, cattle, mice or rat with humans being preferred.

The present invention also envisages a method for preparing a lyophilized solid pharmaceutical composition (adapted for intravenous administration) comprising a) a compound having the formula (I):

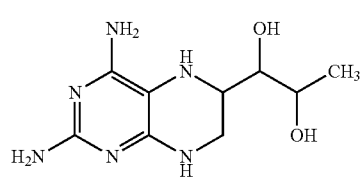

and/or a compound having the formula (II):

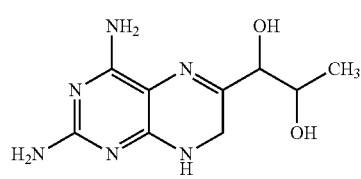

and b) at least one phosphate salt and optionally NaCl;

the method comprising:

aa) dissolving the compound of the formula (III) and/or (II):

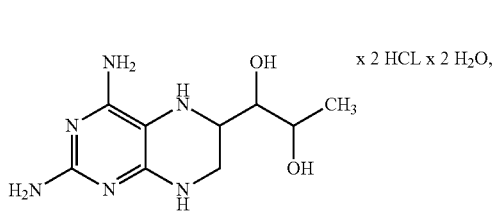

or

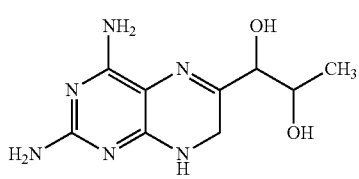

with a buffer, wherein preferably the buffer comprises the phosphate; and bb) lyophilization of the solution obtained in aa).

In this context, it is noted that while the compound of formula (II) is readily available as such from synthesis, the typical synthesis product of the compound of formula (I) is its dihydrochloride dihydrate shown in formula (III). For this reason, in the method of preparing a solid composition of the invention that contains the compound of formula (I), 4-Amino-5,6,7,8-tetrahydro-L-biopterin, the starting material is typically 4-Amino-5,6,7,8-tetrahydro-L-biopterin dihydrochloride dihydrate, the compound of formula (III).

Also, the present invention further relates to a method for preparing a lyophilized solid pharmaceutical composition (adapted for intravenous administration) comprising a) a compound having the formula (I):

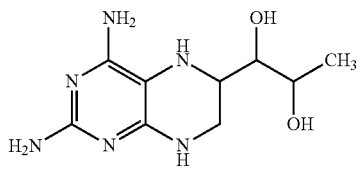

and/or a compound having the formula (II):

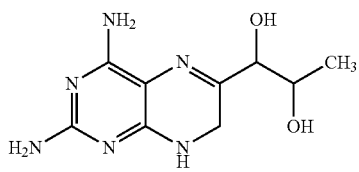

and b) at least one inorganic acid, preferably NaCl;

the method comprising:

aa) dissolving the compound of the formula (III) and/or of the formula (II):

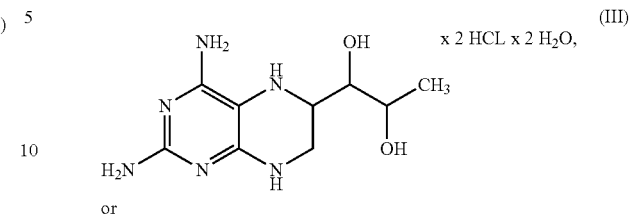

or

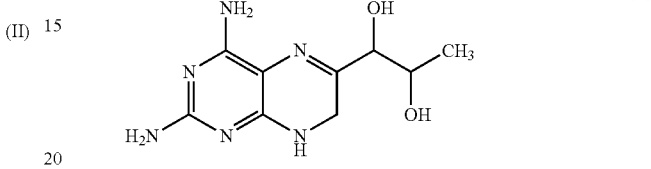

with a buffer;

bb) lyophilisation of the solution obtained in aa).

The buffer as described in aa) is used to dissolve the compound of the formula (III) and/or of the formula (II) to give a compound-buffer solution. A buffer, in general, is a solution which contains a weak acid (or a base) and the salt of that weak acid (or that base). Further, it resists changes in pH when small quantities of an acid or an alkali are added to it. Various phosphates may form several different buffer combinations. Three possible sodium phosphates may include $NaH_2PO_4$—sodium dihydrogen phosphate, $Na_2HPO_4$—disodium hydrogen phosphate, $Na_3PO_4$—sodium phosphate.

The buffer in aa) can also be a sodium hydrogen phosphate buffer comprising at least one phosphate salt. A "sodium hydrogen phosphate buffer" is a buffer comprising a sodium phosphate salt. In some embodiments, the sodium phosphate buffer comprises at least one sodium phosphate salt as described above. In other embodiments, the sodium phosphate buffer comprises 2, 3, 4, 5, or more sodium phosphate salts, preferably the two different phosphate salts as described above. In another embodiment of the method of the present invention, the sodium hydrogen phosphate buffer is prepared by separately dissolving $NaH_2PO_4.2H_2O$ and $Na_2HPO_4.2H_2O$.

The term "separately dissolving" means that the dissolving of each sodium phosphate is taking place spaced apart from each other, for example in different glassware. In a further embodiment of the method of the present invention, the sodium hydrogen phosphate buffer has a pH of 7.4 by adding the $NaH_2PO_4.2H_2O$ dissolution to the $Na_2HPO_4.2H_2O$ solution.

In addition the buffer in aa) can comprise NaOH, sodium hydrogen phosphate buffer and water. Optionally, the NaOH is a 5N NaOH solution. A "5N NaOH solution" means a solution of NaOH (sodium hydroxide) which has a normality of 5 (5N). If the concentration of a sodium hydroxide solution is c (NaOH)=5 mol/L, then its normality is 5N.

In some embodiments of the method of the present invention the buffer comprises 12-16% (w/w) NaOH 5N, 8-12% (w/w) sodium hydrogen phosphate buffer and 74-78% (w/w) water for injection.

In further embodiments of the method of the present invention, the buffer has a pH of about 8, 9, 10, 11, 12, 13 or 14.

In yet another embodiment of the method of the present invention, the solution in step aa) has a pH of about 4, 5, 6, 7, 8, 9, 10 or 11 preferably between 6.5-7.6, most preferably about 7.4.

The buffer can be prepared in different ways. For example, it can be prepared under degasification to give a degassed buffer. A "degassed buffer" refers to the removal of dissolved gases e.g. oxygen from liquids, especially water or aqueous solutions. Bubbling a solution with an inert gas substitutes the dissolved harmful, reactive gases such as oxygen and carbon dioxide. Nitrogen, argon, helium, and other inert gases are commonly used. To complete the substitution, the solution should be stirred vigorously and bubbled for a long time. In some embodiments, the buffer is degassed with nitrogen until the oxygen content is <1.0 ppm (parts per million).

As a further additional step in the method, the solution obtained in aa) can be sterile filtered, preferably with a 0.22 μm filter. Sterile filtered embraces any process that eliminates (removes) or kills all forms of microbial life, including transmissible agents (such as fungi, bacteria, viruses, spore forms, etc.) present on a surface, contained in a fluid, in medication or in a composition (solid or fluid). Here, sterilization is achieved by filtration. Sterilization can also be achieved by applying heat, chemicals, irradiation, high pressure, or combinations thereof with a filtration step. The filter can have different pore sizes. Usually, a filter with pore size 0.2 μm (microfiltration) will effectively remove microorganisms. In the processing of Biologics, viruses must be removed or inactivated e.g. by heat or glutaraldehyde or the like. Nanofilters with a smaller pore size of 20-50 nm (nanofiltration) are used. The smaller the pore size the lower the flow rate. To achieve higher total throughput or to avoid premature blockage, pre-filters might be used to protect small pore membrane filters.

In another embodiment of the method of the present invention after the preparation of the pharmaceutical composition; the lyophilisation is started at most 2 hours later, preferably at most 1.5 hours later, 1 hour later, 30 minutes later most preferably at most 15 minutes later.

Notably, the present invention also relates to a pharmaceutical composition obtainable by the method of the present invention.

For a better handling of the solid pharmaceutical composition of the present invention the lyophilisate obtained in bb) or the pharmaceutical composition of the present invention is filled into vials, preferably in an amount about 1-1.5 g, preferably about 1.25 g solid formulation. Alternatively, the lyophilisate obtained in bb) or the pharmaceutical composition may be filled into vials in an amount about 0.9-1.4 g, preferably 1.15 g solid formulation. When used as "unit dosage, the amount of about 1-1.5 g, or preferably of about 1.25 g solid formulation, or, alternatively, the amount of about 0.9-1.4 g, preferably 1.15 g solid formulation is filled into a 50 ml vial. The term "vial" refers to a (small) glass or plastic vessel or bottle, often used to store pharmaceutical compositions as liquids or solids. Nowadays, vials are also often made of plastics such as polypropylene or polystyrene. Any other suitable container can of course also be used for the storage of the solid composition of the invention.

To obtain a ready-to use injectable solution, the method of the present invention also comprises the step of reconstituting the lyophilisate obtained in bb) in a pharmaceutically acceptable fluid for the preparation of an injectable solution. The term "injectable solution" refers to a solution that can be utilized for intravenous administration, preferably for injection or infusion (see also above the disclosure for injection).

An injectable solution comprises a pharmaceutically acceptable fluid.

The present invention is further characterized by the following list of items:

Item 1. A solid pharmaceutical composition adapted for intravenous administration comprising
a) a compound having the formula (I):

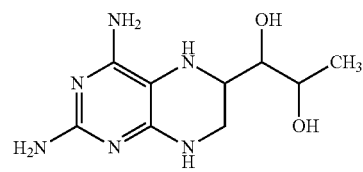

and/or a compound having the formula (II):

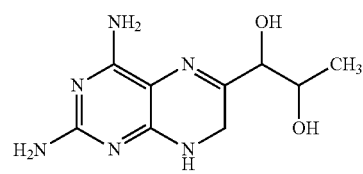

and
b) at least one phosphate salt.

Item 2. The pharmaceutical composition of claim 1, wherein the at least one phosphate salt is a sodium phosphate, a potassium phosphate or an ammonium phosphate.

Item 3. The pharmaceutical composition of item 2, wherein the phosphate salt is selected from the group consisting of $Na_2HPO_4$ (water free), $Na_2HPO_4.2H_2O$, $Na_2HPO_4.7H_2O$, $Na_2HPO_4.12H_2O$, $NaH_2PO_4$ (water free), $NaH_2PO_4.H_2O$, $NaH_2PO_4.2H_2O$, $K_2HPO_4$ (water free) $K_2HPO_4.3H_2O$, $KH_2PO_4$ (water free) and mixtures thereof.

Item 4. The pharmaceutical composition of item 2, wherein the phosphate salt is $Na_2HPO_4.2H_2O$ and wherein the quantity of the $Na_2HPO_4.2H_2O$ present in the composition is chosen such that the molar ratio of the $Na_2HPO_4.2H_2O$ to compound (I) or compound (II) ranges from 0.04 to 0.4.

Item 5. The pharmaceutical composition of item 2, wherein the sodium phosphate is $NaH_2PO_4.2H_2O$, and wherein the quantity of the $NaH_2PO_4.2H_2O$ present in the composition is chosen such that the molar ratio of the $NaH_2PO_4.2H_2O$ to compound (I) or compound (II) ranges from 0.01 to 0.09.

Item 6. The pharmaceutical composition of any of items 1-5, comprising two different sodium phosphate salts.

Item 7. The pharmaceutical composition of item 6, wherein the two different sodium phosphate salts are $NaH_2PO_4.2H_2O$ and $Na_2HPO_4.2H_2O$.

Item 8. The pharmaceutical composition of item 7, wherein the quantity of the $NaH_2PO_4.2H_2O$ and $Na_2HPO_4.2H_2O$ present in the composition is chosen such that the molar ratio of both $NaH_2PO_4.2H_2O$ and $Na_2HPO_4.2H_2O$ to compound (I) or compound (ii) ranges from 0.02 to 0.5.

Item 9. The pharmaceutical composition of any of items 1-8, wherein the compound (I) and/or the compound (II) are present as the free base.

Item 10. The pharmaceutical composition of any of items 1-9, wherein the pharmaceutical composition is a lyophilized pharmaceutical composition.

Item 11. The pharmaceutical composition of any of items 1-10, wherein the compound (I) is a compound having the formula (Ia):

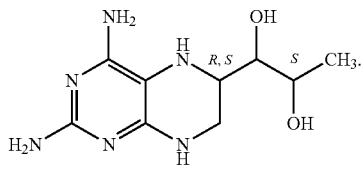

Item 12. The pharmaceutical composition of any of items 1-11, wherein the compound (II) is a compound having the formula (IIa):

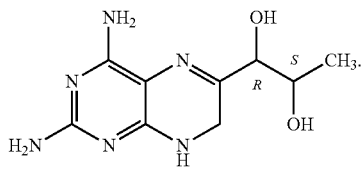

Item 13. The pharmaceutical composition of any of items 1-12, wherein the pharmaceutical composition comprises an additional pharmaceutical excipient.

Item 14. The pharmaceutical composition of item 13, wherein the additional pharmaceutical excipient is an inorganic salt.

Item 15. The pharmaceutical composition of item 14, wherein the inorganic salt is selected from $MgCl_2$, $CaCl_2$, $NH_4Cl$, KCl, or NaCl.

Item 16. The pharmaceutical composition of item 15, wherein the inorganic salt is NaCl.

Item 17. The pharmaceutical composition of item 16, wherein the quantity of the NaCl present in the composition is chosen such that the molar ratio of the NaCl to compound (I) or compound (II) ranges from 1.5 to 4, preferably from 1.8 to 3.7.

Item 18. The pharmaceutical composition of any of items 1-17, wherein the composition further comprises crystallization water.

Item 19. The pharmaceutical composition of any of items 1-18, wherein the composition is adapted to be reconstituted in water.

Item 20. The pharmaceutical composition of any of items 1-19, wherein the composition is adapted for administration by infusion or injection.

Item 21. The pharmaceutical composition of any of items 1-20, wherein the compound (I) is (6R)-4-Amino-5,6,7,8-tetrahydro-L-biopterin.

Item 22. The pharmaceutical composition of any of items 1-21, wherein the compound (I) is (6S)-4-Amino-5,6,7,8-tetrahydro-L-biopterin.

Item 23. The pharmaceutical composition of any of items 1-22, wherein the compound (I) is a diastereomeric mixture that comprises more (6R)-4-Amino-5,6,7,8-tetrahydro-L-biopterin than (6S)-4-Amino-5,6,7,8-tetrahydro-L-biopterin.

Item 24. The pharmaceutical composition of item 23, wherein the quantity of the (6R)-4-Amino-5,6,7,8-tetrahydro-L-biopterin and the (6S)-4-Amino-5,6,7,8-tetrahydro-L-biopterin is chosen such that the ratio of the amount of (6R)-4-Amino-5,6,7,8-tetrahydro-L-biopterin to the (6S)-4-Amino-5,6,7,8-tetrahydro-L-biopterin ranges from 0.5 to 2, preferably around 1.3.

Item 25. The pharmaceutical composition of any of items 1-24, wherein a unit dosage of the composition contains 650±60 mg of the free base of 4-Amino-(6R,S)-5,6,7,8-tetrahydro-L-biopterin, 140±30 mg of water of crystallization, 70±7 mg $Na_2HPO_4.2H_2O$, 16.5±2 mg $NaH_2PO_4.2H_2O$, and 350±30 mg NaCl.

Item 26. The composition of any of items 1-25, wherein the composition comprises 1, 2, 3, 4, 5, 6, 7, or more additional compounds, wherein the additional compounds are selected from the group consisting of one or more of the compounds selected from the group consisting of 4-Amino-L-biopterin, (6R,S)-5,6,7,8-Tetrahydro-L-biopterin, 1-[(6R,S)-2,4-Diamino-5,6,7,8-tetrahydropteridin-6-yl]propanol, 1-[(6R,S)-2,4-Diamino-5,6,7,8-tetrahydropteridin-6-yl]propane, (1R,2S)-1-[(6R,S)-2-(Acetylamino)-4-amino-5,6,7,8-tetrahydropterin-6-yl]-1,2-diacetoxy-propane, 2,4-Diamino-7,8-dihydropteridine, 2,4-Diaminopteridine.

Item 27. Use of a lyophilized pharmaceutical composition of any of items 1 to 26 for the treatment of a disease.

Item 28. The use of item 27, wherein the disease is selected from the group consisting of a traumatic brain injury, non-traumatic brain injury, preferably stoke or meningitis, elevated cranial pressure, secondary brain injury.

Item 29. A method for preparing a lyophilized solid pharmaceutical composition adapted for intravenous administration comprising a) a compound having the formula (I):

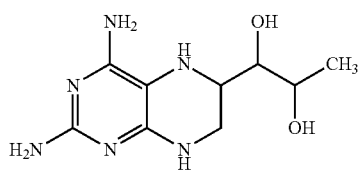

and/or a compound having the formula (II):

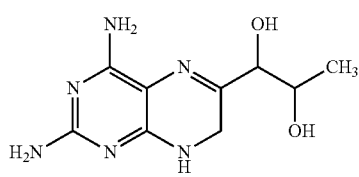

and b) at least one phosphate salt;

the method comprising:

aa) dissolving the compound of the formula (III) and/or (II):

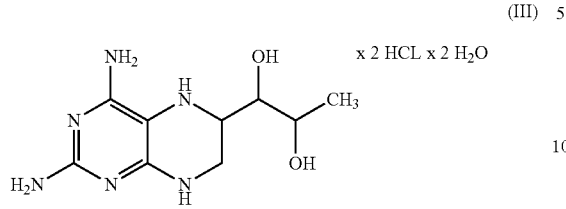

with a buffer;
bb) lyophilization of the solution obtained in aa).

Item 30. The method of item 29, wherein the method further comprises the step of reconstituting the lyophilisate obtained in bb) in a pharmaceutically acceptable fluid for the preparation of an injectable solution.

Item 31. The method of item 29 or 30, wherein the buffer in aa) is a sodium hydrogen phosphate buffer comprising at least one phosphate salt.

Item 32. The method of any of items 29-31, wherein the buffer in aa) comprises NaOH, sodium hydrogen phosphate buffer and water.

Item 33. The method of item 31, wherein the NaOH is a 5N NaOH solution.

Item 34. The method of item 31 wherein the sodium hydrogen phosphate buffer is prepared by separately dissolving $NaH_2PO_4.2H_2O$ and $Na_2HPO_4.2H_2O$.

Item 35. The method of item 33 wherein the sodium hydrogen phosphate buffer has a pH of 7.4 by adding the $NaH_2PO_4.2H_2O$ solution to the $Na_2HPO_4.2H_2O$ dissolution.

Item 36. The method of any of items 29-35, wherein the buffer comprises 12-16% (w/w) NaOH 5N, 8-12% (w/w) sodium hydrogen phosphate buffer and 74-78% (w/w) water for injection.

Item 37. The method of any of items 29-36, wherein the solution obtained in aa) is sterile filtered, preferably with a 0.22 μm filter.

Item 38. The method of any of items 29-37, wherein the buffer has a pH of about 8, 9, 10, 11, 12, 13 or 14.

Item 39. The method of any of items 29-38, wherein the solution in step aa) has a pH of about 4, 5, 6, 7, 8, 9, 10 or 11 preferably between 6.5-7.6, most preferably 7.4.

Item 40. The method of any of items 29-39, wherein the lyophilisate obtained in bb) is filled into vials, preferably in an amount about 1-1.5 g, preferably 1.25 g solid formulation.

Item 41. The method of any of items 29-40, wherein buffer is prepared with degassed buffer.

Item 42. The method of any of items 29-41, wherein buffer is degassed with nitrogen until the oxygen content is <1.0 ppm.

Item 43. The method of any of items 29-42, wherein after the preparation of the solution; the lyophilisation is started at most 2 hours later.

Item 44. Pharmaceutical composition obtainable by the method of any of items 29-43.

Item 45. Use of the lyophilized pharmaceutical composition of any of items 1-28 in the manufacture of a medicament for treating a subject having closed head injury, elevated cranial pressure and secondary brain injury.

Item 46. A method of treating a disease in a subject, comprising the step of administering a lyophilized pharmaceutical composition of any of items 1 to 28 to a subject in need thereof.

Item 47. The method of item 46, wherein the maximal daily dose is 20 mg/kg body weight, preferably, 17.5, 15.0 or 12.5, 10, 8.5, 7.5, 5.0, 2.5 mg/kg body weight.

EXAMPLES

The following examples further illustrate the invention. These examples should however not be construed as to limit the scope of this invention. The examples are included for purposes of illustration and the present invention is limited only by the claims.

Example 1—Description of Manufacturing Process

VAS203 is prepared in a multistep synthesis starting from commercially available L-biopterin. A process scheme is shown in FIG. 1. The synthesis of VAS203 is based on the publications W. Pfleiderer et al. in Pteridines 1989, 1, 199-210 and Pteridines 1995, 6, 1-7.

It was the aim of the first development phase to reproduce the literature procedures and to estimate their feasibility for multi-gram scale. Purification of intermediates by flash-chromatography was eliminated and substituted by precipitation or crystallisation steps. Furthermore, adoptions on molar ratios of reagents and reaction-conditions were performed, so that a robust process up to the intermediate MAE 119 (4-Amino-L-biopterin) was available.

It was problematic to establish a robust and reliable route for the hydrogenation of MAE 119 to VAS203, using PtO2 as catalyst. Different solvents and aqueous media at different pH-values were tested, but only when diluted hydrochloric acid was used, quick and reproducible results, especially on the diastereomeric ratio of the drug substance, could be achieved. The total amount of residual platinum burden could be drastically reduced by pre-hydrogenation of the platinum (IV) oxide catalyst, thereby the diastereomeric ratio changed slightly. Workup of the acidic solution of VAS203 proved to be difficult, since simple evaporation of water at reduced pressure left a glass-like residue. The breakthrough was achieved, when 2-propanol was used as co-solvent for the evaporating process. This procedure yielded a solid, but unfortunately, 2-propanol is incorporated into this solid. By conventional drying-conditions the amount of residual 2-propanol could not be reduced below 5% (w/w). To overcome this problem, a final lyophilisation step to generate VAS203 can be included. Single batches may be pooled to give larger quantities.

Evidence for the structural assignment of VAS203 was provided by the route of synthesis, supported by elemental analysis, nuclear magnetic resonance ($^1$H-NMR and $^{13}$C-NMR), UV and IR spectroscopy (data not shown).

Example 2

Description and Composition of the Drug Product

VAS203 will be supplied as a sterile, white to pale red or brown lyophilised powder filled in 50 mL glass vials under nitrogen as a protective atmosphere. Each vial contains 650±60 mg of the free base of 4-Amino-(6R,S)-5,6,7,8-tetrahydro-L-biopterin and 140±30 mg of water of crystallisation. Additionally, the vials contain 350±30 mg sodium chloride (NaCl), 70±7 mg disodium hydrogen phosphate dihydrate ($Na_2HPO_4.2H_2O$), and 16.5±2 mg sodium dihydrogen phosphate dihydrate ($NaH_2PO_4.2H_2O$). The limits of tolerance of the drug product composition are relatively high (±10%). The reason for this is the variation of the hydrochloride content of VAS203. The hydrochloride content of VAS203 varies from batch to batch up to 10% (from 2.03HCl to 2.24HCl). During the preparation of the drug product the hydrochloride was neutralised in the present invention by addition of sodium hydroxide and sodium-phosphate buffer to obtain an isotonic solution with a physiological pH value. Therefore, also the content of the molecules generated during neutralisation (sodium chloride, disodium hydrogen phosphate and sodium dihydrogen phosphate) varies according to the hydrochloride content of the respective VAS203 batch. The given limits of tolerance are necessary to meet the specifications of the quality relevant parameters pH and osmolality. The qualitative composition of 1 g VAS203 vials is listed in Table 2.

TABLE 2

| Component | Reference to standards | Function |
|---|---|---|
| 4-Amino-(6R,S)-5,6,7,8-tetrahydro-L-biopterin | In house | Active ingredient |
| Sodium chloride* | Ph. Eur. | Osmolarity |
| Disodium hydrogen phosphate dihydrate | Ph. Eur. | Buffer |
| Sodium dihydrogen phosphate dihydrate | Ph. Eur. | Buffer |
| Water for injection (aqua ad inject.) | Ph. Eur. | Solvent used for reconstitution |
| Nitrogen | Ph. Eur. | Protective atmosphere |

*Sodium chloride is generated during the preparation of the formulation when the hydrochloride of the drug substance reacts with the sodium hydroxide solution. Both ingredients comply with the European Pharmacopoeia.

Pharmaceutical Development

A solid lyophilised dosage form is being developed here for VAS203 for the preparation of an infusion solution.

1 g VAS 203 ad 10 g sodium hydroxide/sodium hydrogen phosphate solution buffer with a final pH of 7.4 was selected to be aseptically processed, sterilised by membrane filtration and filled into 50 mL glass vials. Subsequently, this solution was freeze-dried according to a selected lyophilisation program that produced a lyophilised product with excellent stability. In this solid composition, VAS 203 is present as free base 4-Amino-5,6,7,8-tetrahydro-L-biopterin. The vials are closed under nitrogen, sealed with freeze-drying stoppers and closed with white vacuum closures. The excipients are added in order to provide an isotonic solution with physiological pH after reconstitution with 50 mL water ad inject. The pH of the final isotonic solution is 6.5 to 7.6. The final concentration of the drug substance VAS203 is 20 mg/mL.

Description of Manufacturing Process and Process Controls

At a pH of 7.4 4-Amino-(6R,S)-5,6,7,8-tetrahydro-L-biopterin dihydrochloride dihydrate (VAS203) dissolved in solution buffer is very unstable and oxidises in its two metabolites 4-Amino-7,8-dihydro-L-biopterin and 4-Amino-L-biopterin. Therefore, it is important that the VAS203 solution is prepared with degassed buffer and after preparation of the VAS203 solution the lyophilisation should be started without delay.

To allow lyophilisation in 50 mL vials a concentrated VAS203 solution buffer has to be prepared (1 g VAS203 ad 10 g buffer). The solution buffer is prepared by mixing the stock solutions:

14% (w/w) solution of sodium hydroxide (NaOH) 5 N

10% (w/w) solution of sodium hydrogen phosphate buffer (NaPB)

500 mmol/L, pH 7.4

76% (w/w) water for injection

Figure 2:
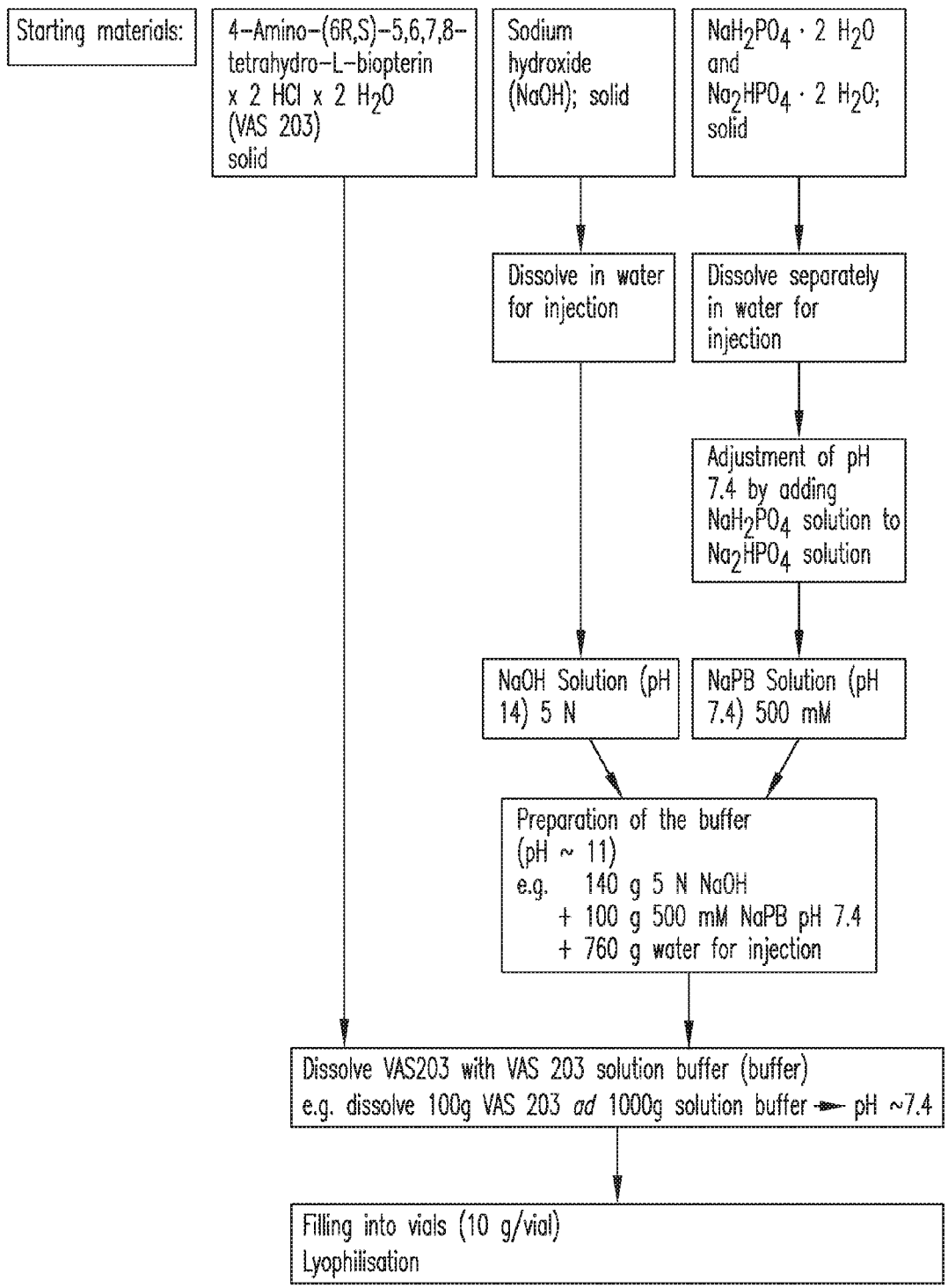
FIG. 2 shows a manufacturing process of VAS203 drug product according to the invention.

The sterile solution buffer is then degassed with nitrogen until the oxygen content is <1.0 ppm. For each vial 9.0 g of this solution buffer is used to dissolve 1.0 g VAS203. The solution buffer is filled into a nitrogen-flushed flask and solid (lyophilized) VAS203 is carefully added within 15 minutes under nitrogen as a protective atmosphere. After check of pH-value the VAS203 solution is sterile filtered with a 0.22 µm Millipak 200 filter. The 0.22 µm filters are integrity tested after use. A sample of 100 mL is taken for testing the bioburden. The bioburden limit of the drug product solution before sterile filtration is defined as =10 cfu/100 mL. The remaining solution is filtered for a second time and dispensed into 50 mL vials, 10 g per vial. The vials are sterilised prior to filling by dry heat according to section 5.1.1. of the European Pharmacopoeia. After the lyophilisation the vials are closed under nitrogen, sealed with freeze-drying stoppers and closed with white vacuum closures. The VAS203 solution is prepared shortly before freeze-drying. The aseptic filling process has been validated using media fill. A flow chart of the successive steps of the manufacturing process, indicating the components used for each step is shown in FIG. 2. The result is a solid composition in which VAS203 is present as free base 4-Amino-(6R,S)-5,6,7,8-tetrahydro-L-biopterin.

Stability

A stability monitoring was carried out for 24 months. Samples were stored "long-term" at 5° C. (verum). An accelerated stability study was carried out at 40° C./75% RH for 6 months (verum). The analytical procedures used in the stability program include tests for assay, purity and related substances. The specifications applied and the methods used are the same as for drug product release.

A stability monitoring was carried out for at least 60 months. Table 3 shows the conditions and the storage period of the stability investigation. Samples were stored "long-term" at 5° C. (verum). An accelerated stability study has been carried out at 40° C./75% RH for 6 months (verum). Table 4 gives the test schedule for the different time points. The analytical procedures used in the stability programme include tests for assay, purity and related substances. The specifications applied and the methods used are the same as for drug product release. Exemplary results of the stability study are shown in Table 5 (which is depicted as FIG. 4).

TABLE 3

Conditions of stability monitoring to be carried out

| Storage Condition | Packaging | Storage Period | Stability Time Points (Months) |
|---|---|---|---|
| 5° C. | 50 mL glass vials | 60 Months | Initial(Release), 3, 6, 9, 12, 18, 24, 36, 48, 60 |
| 40° C./75% RH | 50 mL glass vials | 6 Months | Initial(Release), 1, 3, 6 |

TABLE 4

Test schedule at stability time points

| Month | Condition | Tests to be carried out* |
|---|---|---|
| Initial | — | A |
| 1 | accelerated (40° C.) | B |
| 3 | long-term (5° C.) & accelerated (40° C.) | B |
| 6 | long-term (5° C.) & accelerated (40° C.) | A (accelerated), B (long-term) |
| 9 | long-term (5° C.) | B |
| 12 | long-term (5° C.) | A |
| 18 | long-term (5° C.) | B |
| 24 | long-term (5° C.) | B |
| 36 | long-term (5° C.) | A |
| 48 | long-term (5° C.) | A |
| 60 | long-term (5° C.) | A |

*Tests to be carried out are:
A: Complete shelf-life specification
B: Complete shelf-life specification without test items "sterility", "endotoxins" and "particles"

Discussion

Stability data are available for the batch stored at 5° C. and at 40° C./75% RH, protected from light. Minor changes were observed for samples stored at both temperatures for up to 24 months but these showed no consistent trend and are believed to be within the range of analytical variability. No degradation products were formed. A slight increase could be observed for the first metabolite (oxidation product) of the drug substance (4-Amino-7,8-dihydro-L-biopterin). After 24 months storage at 5° C. in 7 of 10 vials a total of 15 visible particles have been found.

Stability data are available for the batch stored at 5° C. and at 40° C./75% RH, protected from light. No significant changes were detected for samples stored at both temperatures for up to 36 month. No degradation products were formed.

Conclusion

VAS203 drug product vials are stable when stored at 5° C., protected from light, for not less than 36 months. VAS203 drug product vials are stable when stored at 40° C./75% RH, protected from light, for not less than 6 months. Considering the above, a shelf life of 42 months is set for 1 g of lyophilised VAS203 powder filled in 50 mL glass vials under nitrogen as a protective atmosphere. The storage instruction will be to store the vials at 2-8° C., and the vials must be wrapped with aluminium foil and packed in cardboard boxes to protect them from light. All reconstituted drug products should be inspected visually for particulate matter. The storage instruction will be to store the vials at 2-8° C.

The shelf-life may be extended if appropriate long-term and accelerated stability data from the concurrent stability study for 1 g VAS203 vials and 50 mL placebo vials are available and the results meet the current specifications. The shelf-life will be determined according to the principles described in the ICH Q1E guidance:

If no significant change is detected at accelerated conditions over 6 months and long term data show little or no change over time and low variability, twice the period covered by real time data will be used as the extended shelf life, but the shelf life may not exceed the length of available long-term data by more than 12 months.

Example 3—Stability During Preparation for Administration and the Course of the Infusion A stability study at room temperature was carried out for the drug substance VAS203 to test for any degradation of the reconstituted solution in transparent 50 mL polypropylene (PP) syringes which are used in clinical studies. During stability testing the PP syringes were exposed to normal day-light. Solution content, purity, related substances and pH were monitored for 48 hours (initial, 6, 24, 48 hours after preparation). Table 6 displays the results of the stability test.

Discussion

The solution content (assay) remained constant within specified limits (650±60 mg) for 48 hours. During the tested period, the chromatographic purity for both diastereomers was well within specified limits, no significant change could be observed. The relative content of related substances remained constant within specified limits for 48 hours. No degradation products were formed. A slight increase could be observed for the first metabolite of VAS203 (4-Amino-7,8-dihydro-L-biopterin). However, this oxidation was possibly caused by residual oxygen in the syringe, between 6 and 48 hours the change was insignificant. The pH of reconstituted VAS203 solution remained constant within specified limits for 48 hours. No change could be observed. Light sensitivity was not observed up to 48 hours.

Conclusion

Investigations carried out demonstrate that a reconstituted solution of VAS203 is stable in its application device (50 mL PP syringe) at room temperature exposed to normal daylight for 48 hours. However, use-by date was reduced to avoid microbiological contamination. Use-by date was defined as time point of preparation of the VAS203 solution plus 27 hours.

TABLE 6

Stability of reconstituted solution of VAS203 in 50 mL PP syringe (application device), stored at room temperature

| Test Item | Specification (phase I clinical batch) | Storage Period in hours | | | |
|---|---|---|---|---|---|
| | | 0 | 6 | 24 | 48 |
| Assay (HPLC) (calculated on anhydrous and chloride-free basis) Purity (HPLC) | 650 ± 60 mg | 615 mg | 610 mg | 621 mg | 626 mg |
| (6R)-4-Amino-5,6,7,8-tetrahydro-L-biopterin [% area] | 57.0 ± 3.5 | 55.5 | 55.4 | 55.4 | 55.5 |
| (6S)-4-Amino-5,6,7,8-tetrahydro-L-biopterin [% area] | 37.5 ± 3.5 | 39.0 | 38.5 | 38.4 | 38.1 |

TABLE 6-continued

Stability of reconstituted solution of VAS203 in 50 mL PP syringe (application device), stored at room temperature

| Test Item | Specification (phase I clinical batch) | Storage Period in hours | | | |
|---|---|---|---|---|---|
| | | 0 | 6 | 24 | 48 |
| Related substances (HPLC)*: | | | | | |
| A [% area] | ≤4.5 | 3.3 | 3.8 | 3.8 | 4.1 |
| B [% area] | ≤1.2 | 0.6 | 0.6 | 0.6 | 0.6 |
| C [% area] | ≤2.7 | 1.5 | 1.6 | 1.5 | 1.5 |
| Further related substances, each [% area] | ≤0.6 | 0.2 | 0.2 | 0.2 | 0.1 |
| Further related substances, total [% area] | ≤3.0 | 0.5 | 0.6 | 0.6 | 0.4 |
| Reconstituted Solution§ | | | | | |
| pH | 6.5 to 7.6 | 7.1 | N.T. | 7.1 | 7.1 |

N.T.: Not Tested;
§Reconstituted in 50 mL WFI
*A: 4-Amino-7,8-dihydro-L-biopterin; B: Σ (6R)-5,6,7,8-Tetrahydro-L-biopterin and (6S)-5,6,7,8-Tetrahydro-L-biopterin; C: Σ 1-[(6R)-2,4-Diamino-5,6,7,8-tetrahydropteridin-6-yl]propanol and 1-[(6S)-2,4-Diamino-5,6,7,8-tetrahydropteridin-6-yl]propanol It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

What is claimed is:

1. A method of treating a disease in a subject, comprising the step of administering to a subject in need thereof a solid pharmaceutical composition comprising
   a) a compound having the formula (I):

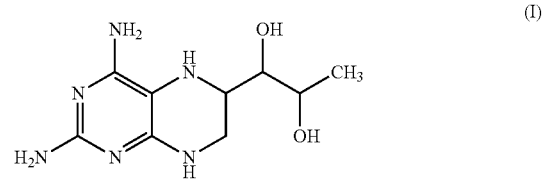 [SMILES: CC(O)C(O)C1CNc2nc(N)nc(N)c2N1]

and/or a compound having the formula (II):

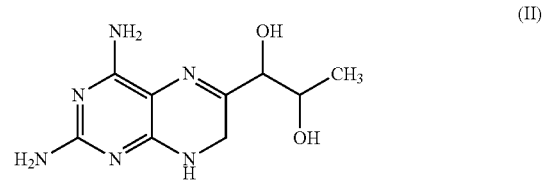 [SMILES: CC(O)C(O)C1=Nc2c(N)nc(N)nc2NC1]

and
   b) two different sodium phosphate salts, wherein the two different sodium phosphate salts are NaH$_2$PO$_4$.2H$_2$O and Na$_2$HPO$_4$.2H$_2$O, and wherein the quantity of the NaH$_2$PO$_4$.2H$_2$O and Na$_2$HPO$_4$.2H$_2$O present in the composition is chosen such that the molar ratio of both NaH$_2$PO$_4$.2H$_2$O and Na$_2$HPO$_4$.2H$_2$O to compound (I) or compound (II) ranges from 0.02 to 0.5, wherein the disease is selected from the group consisting of traumatic brain injury, non-traumatic brain injury, elevated cranial pressure, and secondary brain injury.

2. The method of claim 1, wherein the compound (I) and/or the compound (II) are present as the free base.

3. The method of claim 1, wherein the pharmaceutical composition comprises an additional pharmaceutical excipient.

4. The method of claim 3, wherein the additional pharmaceutical excipient is an inorganic salt.

5. The method of claim 4, wherein the inorganic salt is NaCl.

6. The method of claim 1, wherein the composition further comprises crystallization water.

7. The method of claim 1, wherein a unit dosage of the composition contains 650±60 mg of the free base of 4-Amino-(6R,S)-5,6,7,8-tetrahydro-L-biopterin or of 4-Amino-7,8-dihydro-L-biopterin, 140±30 mg of water of crystallization, 70±7 mg $Na_2HPO_4.2H_2O$, 16.5±2 mg $NaH_2PO_4.2H_2O$, and 350±30 mg NaCl.

8. The method of claim 1, wherein the non-traumatic brain injury is stroke or meningitis.

9. The method of claim 1, wherein the pharmaceutical composition is a lyophilized pharmaceutical composition.

10. The method of claim 9, comprising reconstituting the lyophilized pharmaceutical composition in a pharmaceutically acceptable fluid to form an injectable solution.

11. The method of claim 9, wherein the injectable solution is administered to the subject by infusion or injection.

12. The method of claim 1, wherein the compound having the formula (I) or formula (II) is administered at a maximal daily dose selected from the group consisting of about 10 mg/kg body weight, about 8.5 mg/kg body weight, about 7.5 mg/kg body weight, about 5.0 mg/kg body weight, and about 2.5 mg/kg body weight.

13. The method of claim 1, wherein the compound (I) is (6R)-4-Amino-5, 6, 7, 8-tetrahydro-L-biopterin.

14. The method of claim 1, wherein the compound (I) is (6S)-4-Amino-5, 6, 7, 8-tetrahydro-L-biopterin.

15. The method of claim 1, wherein the compound (I) is a diastereomeric mixture that comprises more (6R)-4-Amino-5, 6, 7, 8-tetrahydro-L-biopterin than (6S)-4-Amino-5, 6, 7, 8-tetrahydro-L-biopterin.

16. The method of claim 15, wherein the quantity of the (6R)-4-Amino-5, 6, 7, 8-tetrahydro-L-biopterin and the (6S)-4-Amino-5, 6, 7, 8-tetrahydro-L-biopterin is chosen such that the ratio of the amount of (6R)-4-Amino-5, 6, 7, 8-tetrahydro-L-biopterin to the (6S)-4-Amino-5, 6, 7, 8-tetrahydro-L-biopterin ranges from 1.1:1 to 2:1.

17. The method of claim 1, wherein the subject is a human.

* * * * *